United States Patent
Wolter et al.

(10) Patent No.: US 10,605,740 B2
(45) Date of Patent: Mar. 31, 2020

(54) PORTABLE ORGANIC MOLECULAR SENSING DEVICE AND RELATED SYSTEMS AND METHODS

(71) Applicant: Aterica Inc., Kitchener (CA)

(72) Inventors: Heinz Wolter, Linwood (CA); Alexander Leyn, Kitchener (CA); Michael Fisher, Waterloo (CA); Erik Helge Borg, Stockholm (SE); Christopher Osuch, Stratford (CA); Gregory John Adams Vilk, Lethbridge (CA); Evan Wright, Guelph (CA); Darian Blanchard, Drumbo (CA)

(73) Assignee: Aterica Inc., Kitchener (CA)

( * ) Notice: Subject to any disclaimer, the term of this patent is extended or adjusted under 35 U.S.C. 154(b) by 167 days.

(21) Appl. No.: 15/794,070

(22) Filed: Oct. 26, 2017

(65) Prior Publication Data
US 2018/0073986 A1 Mar. 15, 2018

Related U.S. Application Data

(63) Continuation of application No. PCT/CA2016/050492, filed on Apr. 28, 2016.
(Continued)

(51) Int. Cl.
*B01L 3/00* (2006.01)
*G01N 1/02* (2006.01)
(Continued)

(52) U.S. Cl.
CPC .......... *G01N 21/77* (2013.01); *B01L 3/508* (2013.01); *B01L 3/527* (2013.01); *G01N 1/02* (2013.01);
(Continued)

(58) Field of Classification Search
CPC .......... B01L 2200/10; B01L 2300/044; B01L 2300/0672; B01L 2300/0832;
(Continued)

(56) References Cited

U.S. PATENT DOCUMENTS 3,992,150 A 11/1976 Retzer
3,996,001 A 12/1976 Sanz et al.
(Continued)

FOREIGN PATENT DOCUMENTS

DE 102014001284 B3 1/2015
EP 2302029 A1 3/2011
(Continued)

OTHER PUBLICATIONS

Document relating to International Application No. PCT/CA2016/050492, dated Jul. 20, 2016 (International Search Report and The Written Opinion).
(Continued)

*Primary Examiner* — Jennifer Wecker
(74) *Attorney, Agent, or Firm* — Bereskin & Parr LLP/S.E.N.C.R.L., s.r.l.

(57) ABSTRACT

A portable device for detecting an analyte associated with a target organic molecule in a liquid and/or solid substance. The device includes a test chamber, a probe, and a sensor. The test chamber contains a liquid volume of test solution including an analytical reagent selected to react with the analyte. The test chamber is sealed by a pierceable membrane wall. The probe is removably positionable to pierce the membrane wall to deposit a sample in the test chamber to form a test mixture with the test solution. The sensor is positioned to detect one or more characteristics of the test mixture in the test chamber indicative of a reaction between the analyte and the analytical reagent.

20 Claims, 27 Drawing Sheets

Related U.S. Application Data

(60) Provisional application No. 62/153,922, filed on Apr. 28, 2015.

(51) Int. Cl.
| | |
|---|---|
| *G01N 21/31* | (2006.01) |
| *G01N 21/66* | (2006.01) |
| *G01N 35/10* | (2006.01) |
| *G01N 1/38* | (2006.01) |
| *G01N 21/77* | (2006.01) |
| *G01N 21/85* | (2006.01) |
| *G01N 33/02* | (2006.01) |
| *G01N 21/76* | (2006.01) |
| *G01N 21/03* | (2006.01) |
| *G01N 21/88* | (2006.01) |

(52) U.S. Cl.
CPC ........... *G01N 1/38* (2013.01); *G01N 21/0303* (2013.01); *G01N 21/314* (2013.01); *G01N 21/66* (2013.01); *G01N 21/76* (2013.01); *G01N 21/763* (2013.01); *G01N 21/8507* (2013.01); *G01N 33/02* (2013.01); *G01N 35/1079* (2013.01); *B01L 2200/10* (2013.01); *B01L 2300/044* (2013.01); *B01L 2300/0672* (2013.01); *B01L 2300/087* (2013.01); *B01L 2300/0832* (2013.01); *G01N 2021/0321* (2013.01); *G01N 2021/0325* (2013.01); *G01N 2021/7756* (2013.01); *G01N 2021/7759* (2013.01); *G01N 2021/8845* (2013.01); *G01N 2201/0221* (2013.01); *G01N 2201/0256* (2013.01)

(58) Field of Classification Search
CPC .... B01L 2300/087; B01L 3/508; B01L 3/527; G01N 1/02; G01N 1/38; G01N 2021/0321; G01N 2021/0325; G01N 2021/7756; G01N 2021/7759; G01N 2021/8845; G01N 21/0303; G01N 21/314; G01N 21/66; G01N 21/76; G01N 21/763; G01N 21/77; G01N 21/8507; G01N 2201/0221; G01N 2201/0256; G01N 33/02; G01N 35/1079

See application file for complete search history.

(56) References Cited

U.S. PATENT DOCUMENTS

| | | | |
|---|---|---|---|
| 5,658,531 | A | 8/1997 | Cope et al. |
| 5,972,713 | A | 10/1999 | Kuzuhara et al. |
| 6,055,050 | A | 4/2000 | Skiffington |
| 9,939,432 | B2* | 4/2018 | Sundvor .............. G01N 33/521 |
| 2005/0221281 | A1 | 10/2005 | Ho |
| 2011/0020178 | A1 | 1/2011 | Clinton et al. |
| 2014/0004548 | A1* | 1/2014 | Gordon ................ B01L 3/5029 |
| | | | 435/21 |
| 2014/0295578 | A1 | 10/2014 | Tan et al. |
| 2015/0037833 | A1 | 2/2015 | Fisher et al. |
| 2018/0011027 | A1* | 1/2018 | Herzog .................. G01N 21/51 |

FOREIGN PATENT DOCUMENTS

| | | |
|---|---|---|
| GB | 2350421 A | 11/2000 |
| WO | 9703209 A1 | 1/1997 |
| WO | 2012078455 A1 | 6/2012 |
| WO | 2016172800 A1 | 9/2016 |

OTHER PUBLICATIONS

Document relating to European Application No. 16785714.3, dated Sep. 27, 2018. pp. 1-17 (Extended European Search Report).
Document relating to European Application No. 16785714.3, dated Sep. 27, 2019. pp. 1-17 (Extended European Search Report).
Document relating to European Application No. 16785714.3, dated Aug. 30, 2019. pp. 1-9 (European Examination Report).

* cited by examiner

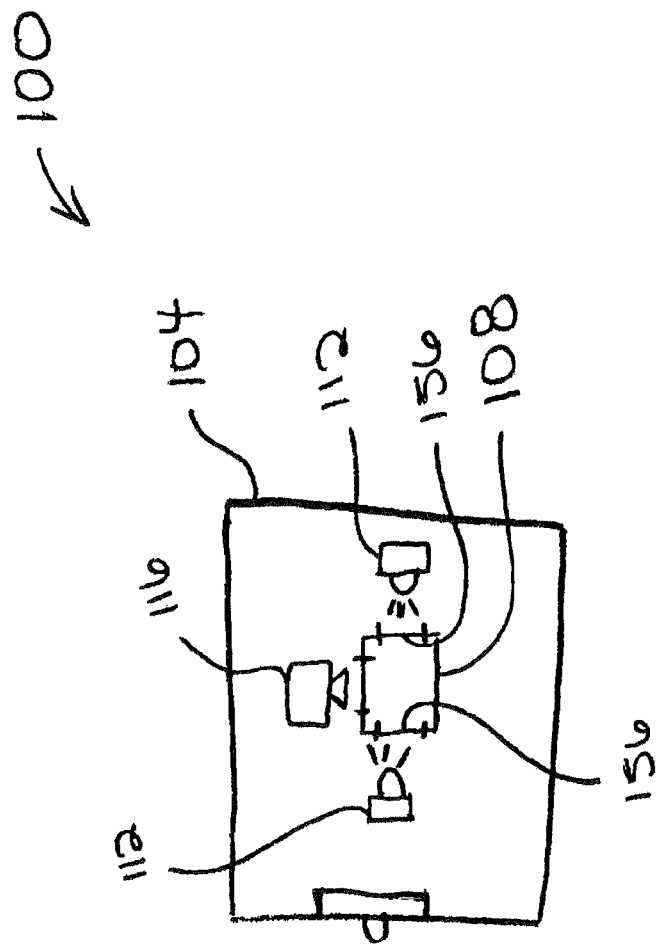

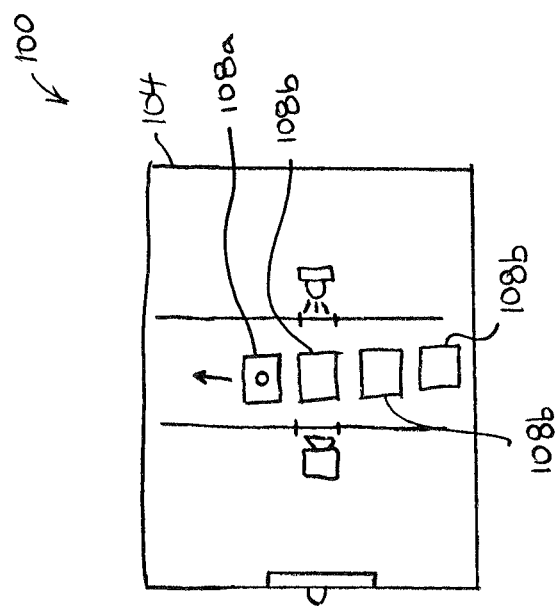

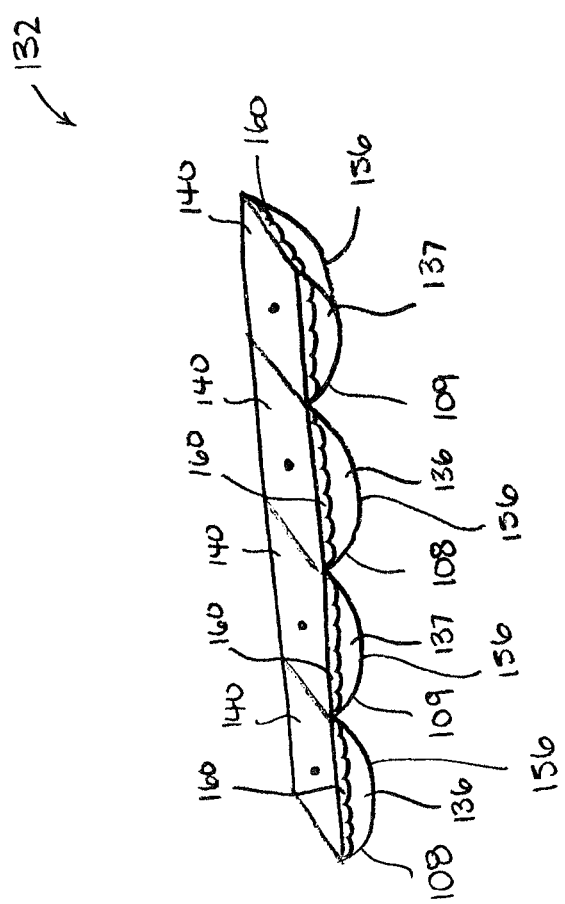

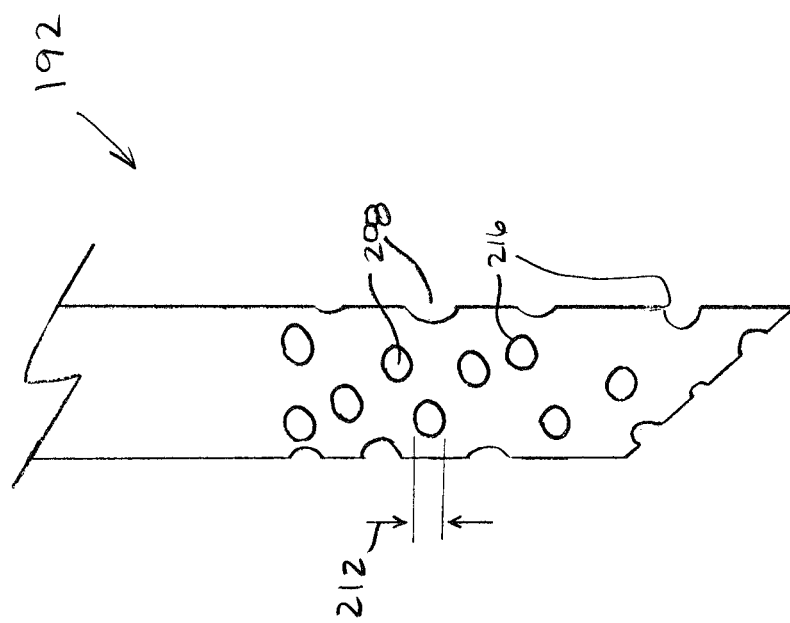

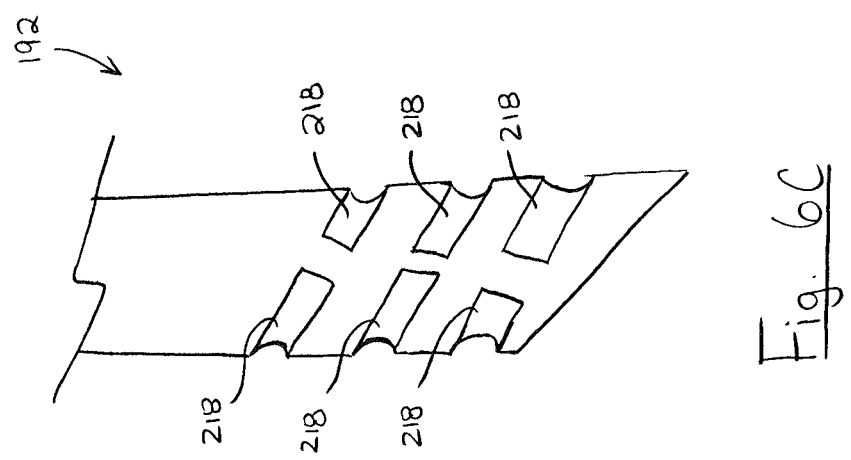

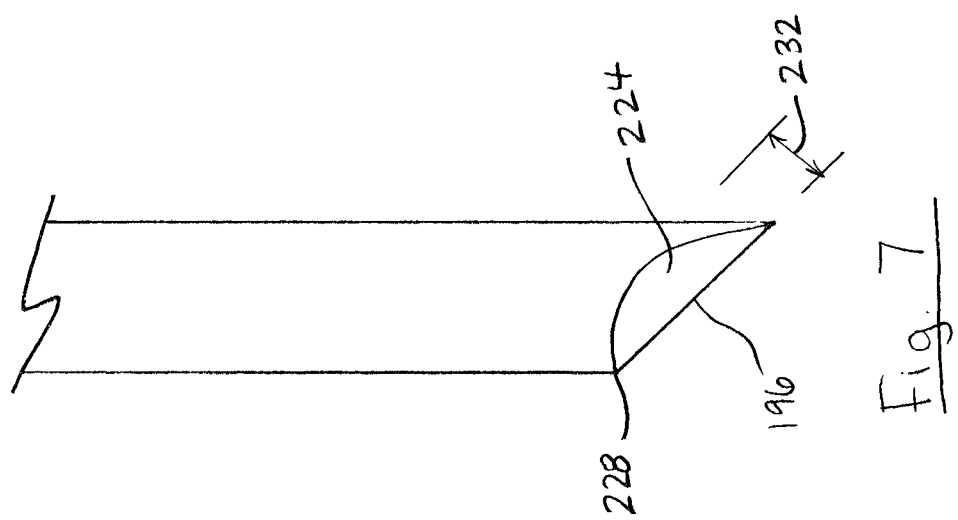

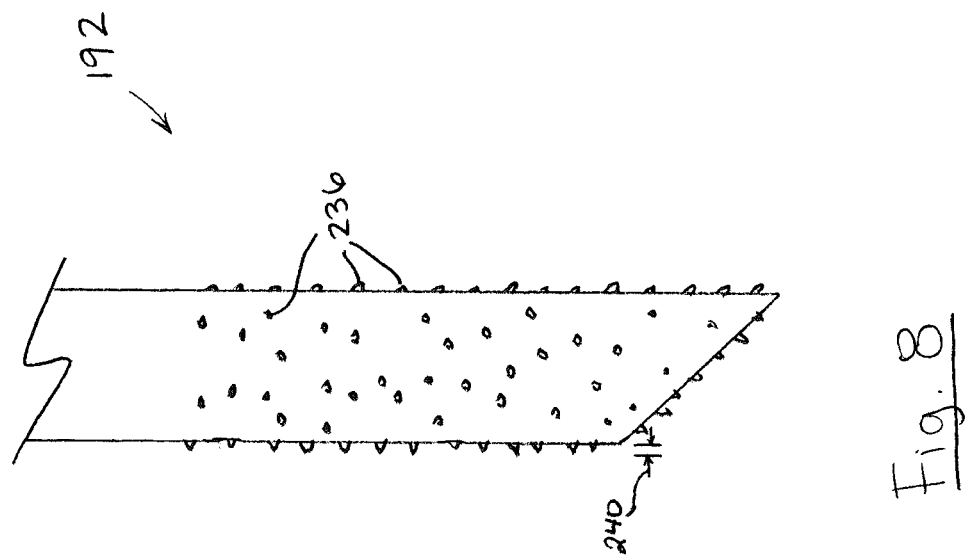

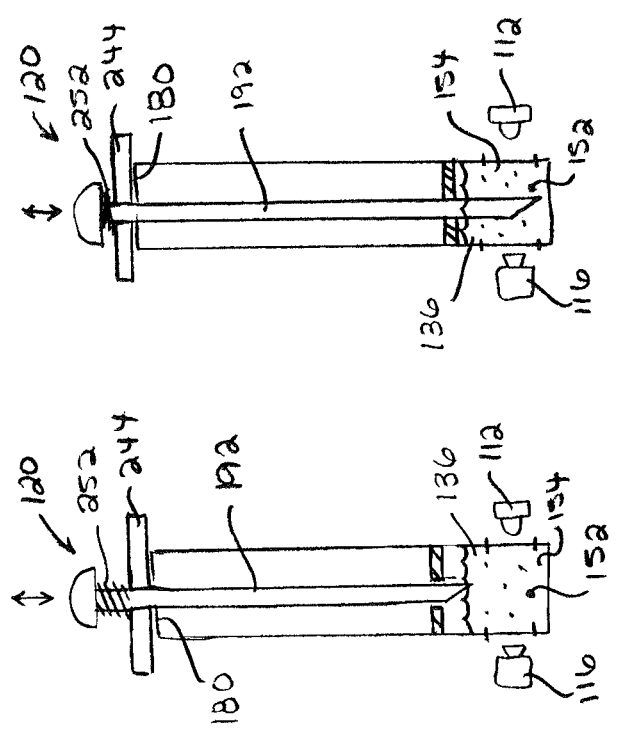

PORTABLE ORGANIC MOLECULAR SENSING DEVICE AND RELATED SYSTEMS AND METHODS

CROSS-REFERENCE TO RELATED APPLICATIONS

This application is a continuation of PCT International Application PCT/CA2016/050492, filed Apr. 28, 2016, which claims the benefit of U.S. Provisional Application No. 62/153,922, filed Apr. 28, 2015. The entire content of PCT Application No. PCT/CA2016/050492 and U.S. Provisional Application No. 62/153,922 are incorporated herein by reference.

FIELD

This disclosure relates to the field of portable devices for organic molecular sensing and related methods.

INTRODUCTION

Millions of individuals live with food allergies and/or food sensitivities. Many food allergies are severe, whereby consumption of the allergen can be life threatening. In some cases, it can be impractical or impossible to obtain a listing of ingredients in food, or the allergy severity makes reliance on an ingredient listing or personal assurance unwise. In these cases, the allergic individual may abstain from eating otherwise safe food, or abstain from the venue or activity altogether.

SUMMARY

In one aspect, a portable device for detecting an analyte associated with a target organic molecule in a liquid and/or solid substance is provided. The device may include a test chamber, a probe, and a sensor. The test chamber may contain a liquid volume of test solution including an analytical reagent selected to react with the analyte. The test chamber may be sealed by a pierceable membrane wall. The probe may be removably positionable to pierce the membrane wall to deposit a sample in the test chamber to form a test mixture with the test solution. The sensor may be positioned to detect one or more characteristics of the test mixture in the test chamber indicative of a reaction between the analyte and the analytical reagent.

In another aspect, a method of detecting an analyte associated with an organic molecule in a liquid and/or solid substance is provided. The method may include piercing the test chamber wall with a probe to deposit a sample from the probe into a liquid volume of test solution including an analytical reagent contained in the test chamber; mixing the sample with the test solution to form a test mixture in the test chamber; and sensing one or more characteristics of the test mixture in the test chamber indicative of a reaction between the analyte and the analytical reagent.

In another aspect, an organic molecular sensing system is provided. The system may include a portable device for detecting an analyte associated with a target organic molecule in a liquid and/or solid substance; and a computing device coupled to the portable device to receive sensor data relating to one or more tests of the substance. The computing device is operable to analyze the sensor data to produce test results corresponding to the presence of the analyte in the substance.

DRAWINGS

FIG. 3B is a schematic of a portable device, in accordance with another embodiment;

FIG. 5 is a schematic of a portable device including a plurality of test chambers;

FIG. 5D is a perspective view of a cartridge including a plurality of test chambers and cleaning chambers;

FIG. 6 is a side elevation view of a portion of a probe shaft that is pitted;

FIG. 6C is a side elevation view of a portion of a probe shaft including a plurality of discontinuously positioned surface channels;

FIG. 7 is a cross-sectional view of a portion of a probe shaft including a distal end cavity;

FIG. 8 is a side elevation view of a portion of a probe shaft including abrasive protrusions;

FIGS. 11 and 12 are cross-sectional views of an inlet passageway, test chamber, and probe, where the probe has a retractable shaft;

DESCRIPTION OF VARIOUS EMBODIMENTS

Numerous embodiments are described in this application, and are presented for illustrative purposes only. The described embodiments are not intended to be limiting in any sense. The invention is widely applicable to numerous embodiments, as is readily apparent from the disclosure herein. Those skilled in the art will recognize that the present invention may be practiced with modification and alteration without departing from the teachings disclosed herein. Although particular features of the present invention may be described with reference to one or more particular embodiments or figures, it should be understood that such features are not limited to usage in the one or more particular embodiments or figures with reference to which they are described.

The terms "an embodiment," "embodiment," "embodiments," "the embodiment," "the embodiments," "one or more embodiments," "some embodiments," and "one embodiment" mean "one or more (but not all) embodiments of the present invention(s)," unless expressly specified otherwise.

The terms "including," "comprising" and variations thereof mean "including but not limited to," unless expressly specified otherwise. A listing of items does not imply that any or all of the items are mutually exclusive, unless expressly specified otherwise. The terms "a," "an" and "the" mean "one or more," unless expressly specified otherwise.

As used herein and in the claims, two or more parts are said to be "coupled", "connected", "attached", or "fastened" where the parts are joined or operate together either directly or indirectly (i.e., through one or more intermediate parts), so long as a link occurs. As used herein and in the claims, two or more parts are said to be "directly coupled", "directly connected", "directly attached", or "directly fastened" where the parts are connected in physical contact with each other. As used herein, two or more parts are said to be "rigidly coupled", "rigidly connected", "rigidly attached", or "rigidly fastened" where the parts are coupled so as to move as one while maintaining a constant orientation relative to each other. None of the terms "coupled", "connected", "attached", and "fastened" distinguish the manner in which two or more parts are joined together.

As used herein and in the claims, a first element is said to be "received" in a second element where at least a portion of the first element is received in the second element, unless specifically stated otherwise.

Figure 1:
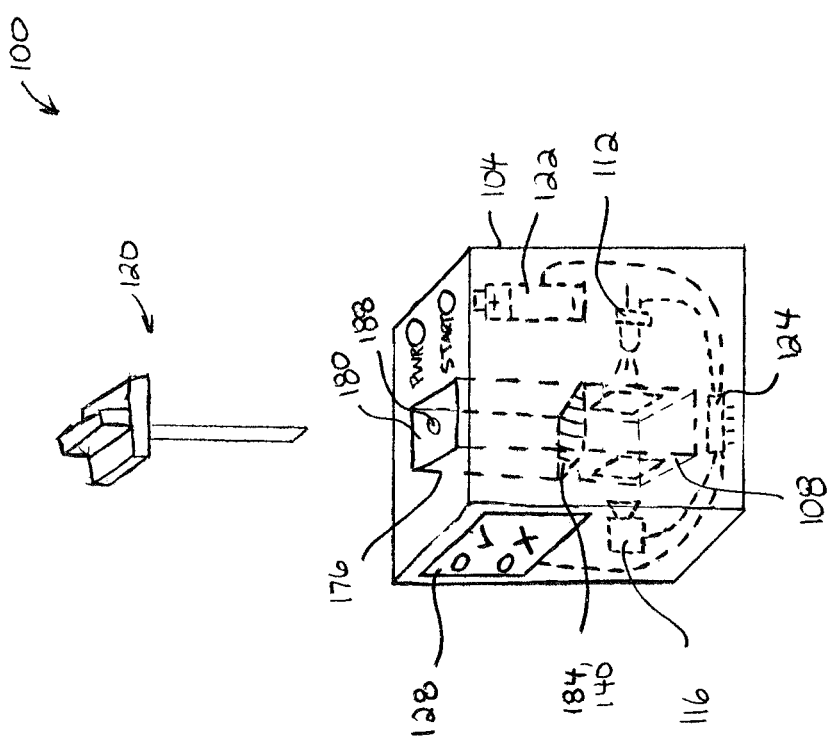
FIG. 1 is a perspective view of a portable device, in accordance with at least one embodiment.

Referring to FIG. 1, a portable device 100 is shown in accordance with at least one embodiment. Device 100 is a portable device for testing liquid and/or solid substances (e.g. consumable products such as food) for a target organic molecule (e.g. allergens) by detecting the presence of an associated analyte in a sample of that substance. The portability of device 100 allows a user to carry the device 100 with them to, e.g. a restaurant or party, and test samples (e.g. food) on-the-fly (e.g. substantially instantaneously) prior to use (e.g. consumption). In the context of foods and food allergies, this can free users burdened with severe allergies to engage in social activities and consume foods they might otherwise avoid. Near-instantaneous testing can make food testing less conspicuous and thereby remove some of the stigma associated with allergies.

As shown, device 100 includes a body (i.e. housing) 104 containing a test chamber 108, a light source 112, and an optical sensor 116. A probe 120 allows a user to collect a sample, and deposit the sample into the test chamber 108 for testing using the light source 112 and optical sensor 116. A battery 122 provides power for the light source 112 and optical sensor 116. In some cases, device 100 includes a processor 124 to receive a readout from optical sensor 116 and assess whether an analyte associated with a target organic substance is present in the deposited sample. Alternatively, or in addition, processor 124 communicates (wirelessly or by wire) the readout from optical sensor 116 to an computing device (e.g. smartphone) for analysis. As shown, device 100 may include a display 128 that is controllable to indicate the results of the test.

Figure 2:
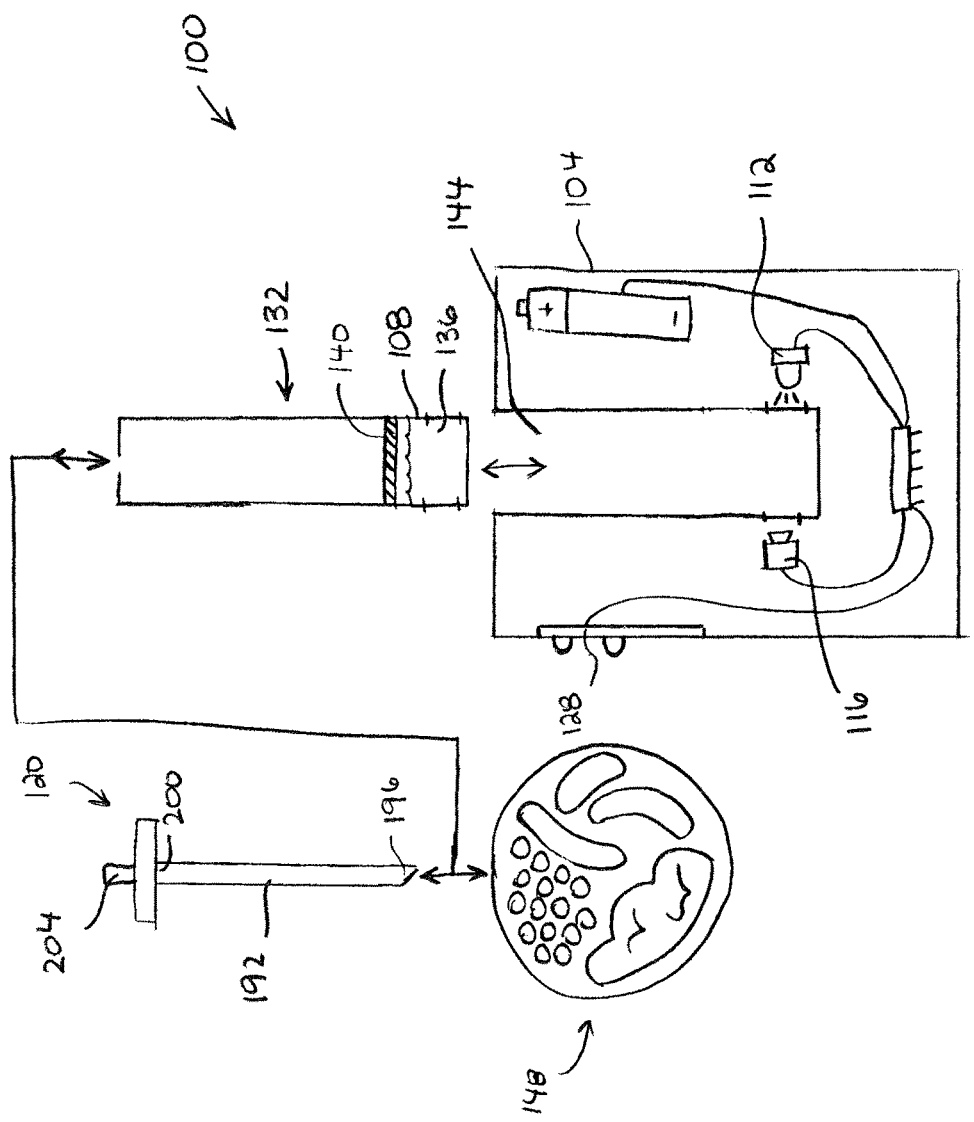
FIG. 2 is a schematic of a portable device and a plate of food, in accordance with another embodiment.
Figure 3:
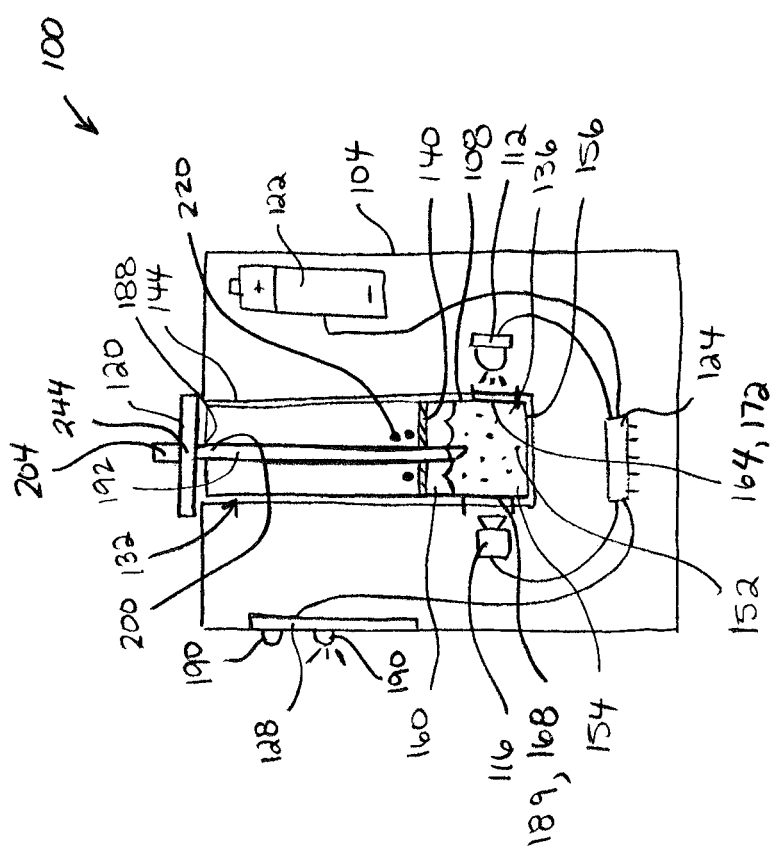
FIG. 3 is a schematic of the portable device of FIG. 2, with a cartridge inserted.

Turning to FIGS. 2 and 3, portable device 100 is shown including a removable cartridge 132 containing test chamber 108. As shown, test chamber 108 includes a test solution 136 including an analytical reagent and a pierceable membrane wall 140. The cartridge 132 is removably insertable into a reception cavity 144 of body 104, whereby the test chamber 108 is aligned to receive optical radiation from light source 112, and to emit optical radiation to optical sensor 116.

In brief, probe 120 is pierced into a product 148 (e.g. food) to collect liquid and/or solid food samples on or in probe 120, and then probe 120 is used to pierce membrane wall 140 whereby samples 152 on probe 120 mix with test solution 136 to produce a test mixture 154. Light source 112 illuminates the test mixture 154 with optical radiation having one or more first wavelengths (e.g. 250 nm), and optical sensor 116 detects optical radiation having one or more second wavelengths (e.g. 450 nm) indicative of the presence of an analyte associated with a target organic substance (e.g. allergen). A readout from optical sensor 116 is assessed to determine whether the sample 152 contains the analyte, and the results are displayed on display 128. The cartridge 132 may then be disposed and replaced with a new cartridge for a subsequent test.

In the embodiments below, substance 148 is described as food (e.g. consumable products), and samples 152 as food samples. However, it is expressly contemplated that embodiments of portable device 100 may be used in connection with other liquid and/or solid substances such as medications, organic compounds, proteins, and other cellular matter. Further, some embodiments of portable device 100 below are described by example as detecting allergens. However, it is expressly contemplated that portable device 100 may be employed to detect other organic molecules such as medications, specific allergens or other triggers of food sensitivities, bacterial byproducts, diagnostically specific analytes, cancer markers, and other cellular matter.

Light source 112 is an example of an excitation source that emits optical radiation, and optical sensor 116 is an example of a sensor that detects optical radiation. In other embodiments, light source 112 and optical sensor 116 may be substituted by or supplemented by one or more other sensing systems, which may sense magnetic field or electrical characteristics for example.

Figure 3D:
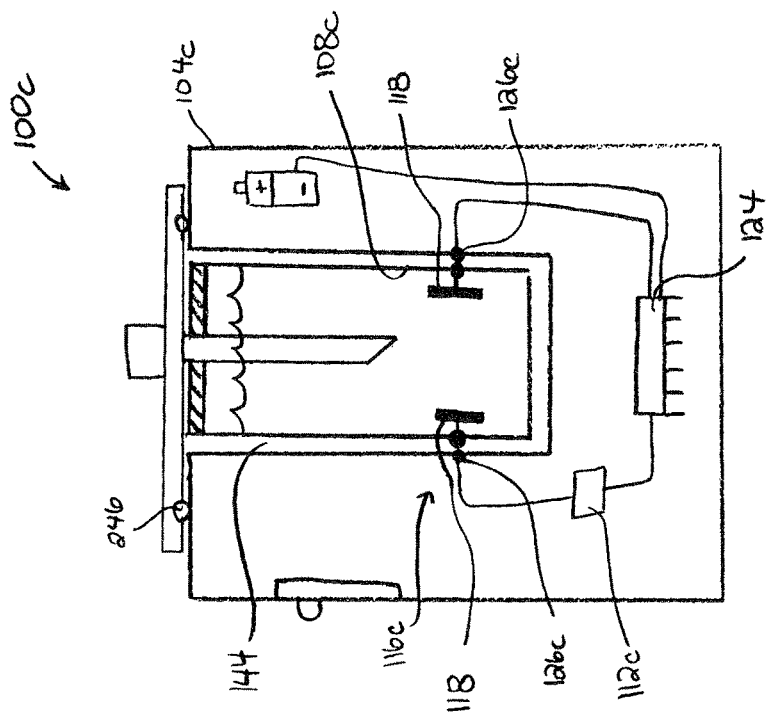
FIG. 3D is a schematic of a portable device, in accordance with another embodiment.
Figure 3C:
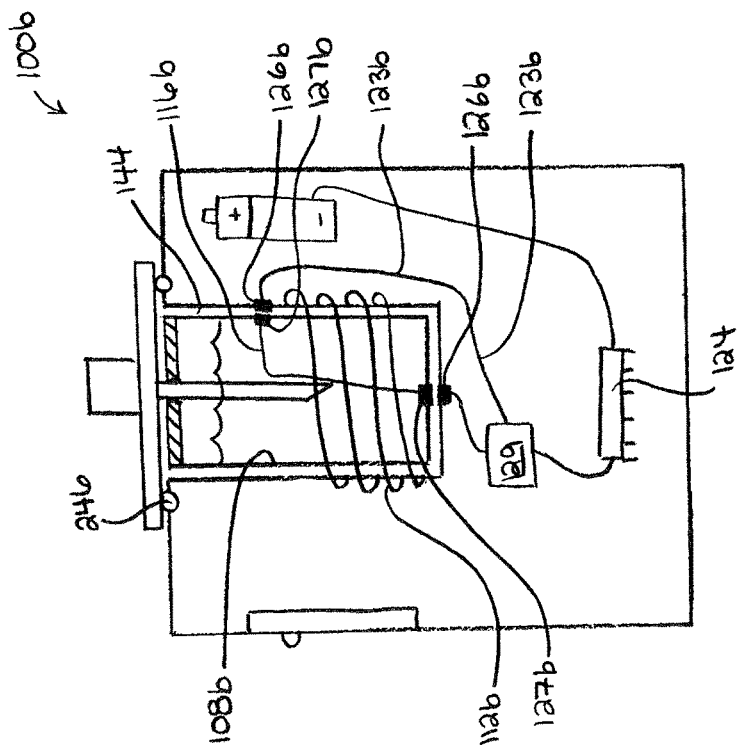
FIG. 3C is a schematic of a portable device, in accordance with another embodiment.

FIG. 3C illustrates an embodiment of portable device 100b including a magnetic sensing system. Portable device 100b has a magnetic field excitation wire (an "excitation source") in the form of an excitation coil 112b and a magnetic field sensing wire 116b. The excitation coil 112b may be wound around the test chamber 108b. The sensing wire 116b may pass through the testing chamber and will typically be electrically isolated from the test mixture, for example, by positioning the sensing wire in a conduit or coating it with a sheath. In device 100b, sensing wire 116b is coupled to conductors 123b through housing contacts 126b and cartridge contracts 127b. Conductors 122b are coupled to processor 124b, optionally through a signal processor 129 such an analog to digital converter. The sensing wire 116b may also be in the form of a coil. More generally, the excitation wire and the sensing wire may be shaped and positioned in any manner that allows a change in the magnetic characteristics of the contents of the test chamber to be sensed. In portable device 100b a magnetic field is induced in test chamber 108b by applying an excitation signal in the form of a current in excitation coil 112*b*. The magnetic field induces a current flow in sensing wire 116*b*. The magnetic coupling between excitation coil 112*b* and sensing wire 116*b* may vary depending on the magnetic characteristics (such as dielectric characteristics or magnetic permeability) of the contents of the test chamber or its contents, resulting in a change in a signal induced in the sensing wire 116*b*, which may be measured as a change in voltage or current. Processor 124 receives a readout corresponding to the signal measure on the sensing wire 116*b* to determine whether the detected magnetic field or change in the magnetic field (static or temporally patterned) is indicative of a target analyte being present in the test mixture.

FIG. 3D illustrates an embodiment of portable device 100*c* including an electrical sensing system including an electrical sensor 116*c* having plates 118*a* and 118*b*. Plates 118 may be positioned adjacent to, within or on the walls of the reception cavity 144*c*. Changes in electrical characteristics, such as capacitance, reactance or resistance, of the contents of the test chamber 108*c* may be measured between the plates 118. In some embodiments utilizing a removable cartridge 132*c*, plates 118 may be installed within the test chamber 108*c* and electrically coupled to conductors 126*c* within the body 104*c*. The electric sensing system may passively detect electrical characteristics using electrical sensor 116*c* without excitation. Alternatively, the electric sensing system may include and an excitation source 112*c* that applies an electric current or electric field across the test chamber contents. Processor 124 receives readouts from electrical sensor 116*c* to determine whether the detected electrical characteristics or change in electrical characteristics (static or temporally patterned) is indicative of a target analyte being present in the test mixture.

Referring to FIGS. 1, 3C, and 3D, in some embodiments, portable device 100 may include two or more sensing systems. This allows portable device 100 to determine the presence of an analyte by reference to a combination of two or more of detected characteristics, such as optical radiation, magnetic field or electrical characteristics, which may allow or improve the detection of some analytes.

Still referring to FIG. 3, battery 122 may be any one or more energy storage devices suitable for providing electrical power to one or more energy consuming components of portable device 100, such as light source 112, optical sensor 116, processor 124, and display 128. For example, battery 122 may include an alkaline, Ni-CAD, NiMH, or Li-ion battery that may be rechargeable or single-use disposable. Preferably, battery 122 has a small form factor to promote the portability of portable device 100. For example, battery 122 may include one or more conventional AA, AAA, C, D, 9-volt, CR-V3, CR-2032, or similarly sized battery cells of the type normally found in portable consumer electronics (e.g. cameras, smartphones, remote controls, etc.).

Portable device 100 may include any test chamber 108 suitable for storing a liquid volume of analytical reagent, allowing for the deposit of a food sample for mixing with the analytical reagent, and allowing for optical testing of a test mixture of the food sample and analytical reagent inside the test chamber. In the illustrated example, test chamber 108 includes one or more chamber walls 156 defining an interior volume 160 containing test solution 136. At least one wall 140 is formed by a membrane that is pierceable by a probe 120 to deposit a food sample in the test chamber 108. Test chamber 108 may be cuboid as shown or any other regular or irregular shape. For example, test chamber 108 may have a rounded (e.g. semi-spherical) chamber wall 156 sealed by a pierceable wall 140 similar to a medicinal blister pack. Each chamber wall 156 may be rigid or flexible. For example, all chamber walls 156 may be rigid and substantially resistant to piercing, except for membrane wall 140 which may be flexible and susceptible to piercing. This allows test chamber 108 to have a predictable shape for illumination and optical detection.

At least a portion of one or more chamber walls 156 may be transparent or translucent to permit illumination of the test mixture 154 inside and optical detection of target analyte(s) associated with a target organic molecule (e.g. allergen). In the illustrated example, chamber walls 156 include an illumination window 164 and a sensor window 168. Each of illumination window 164 and sensor window 168 is at least partially transparent to allow optical radiation of at least target wavelengths to enter and exit test chamber 108 respectively. In some embodiments, one or both of illumination window 164 and sensor window 168 includes an optical filter to block the passage of certain optical radiation wavelengths in accordance with the test protocol. For example, the test protocol may include illuminating the test mixture 154 with optical radiation having a first wavelength, and detecting optical radiation having a second wavelength indicative of the presence of a target analyte in the food sample 152. In this case, if light source 112 additionally emits optical radiation at the second wavelength, then illumination window 164 may include an optical filter 172 to block the optical radiation of the second wavelength. This can help prevent a false positive caused by detecting optical radiation emitted directly by the light source 112 instead of by or through the test mixture 154. In other embodiments, optical filter 172 may be formed in body 104 between light source 112 and test chamber 108. For example, a portion of reception cavity 144 may include optical filter 172 instead of or in addition to illumination window 164.

Illumination window 164 and sensor window 168 may be discrete and spaced apart portions of chamber walls 156 as shown in FIG. 1, or they may be contiguous, overlapping, or even coterminous. In the illustrated example, sensor window 168 is positioned opposite and facing illumination window 164. This allows optical radiation directed into test chamber 108 through illumination window 164 to pass directly through the test mixture 154 inside to the sensor window 168. This may improve the sensitivity of optical sensor 116 by reducing the attenuation of optical radiation passing through test chamber 108 to sensor window 168. In alternative embodiments, sensor window 168 and illumination window 164 may not face each other so as to prevent direct passage of optical radiation from light source 112 to optical sensor 116, in accordance with the test protocol. For example, sensor window 168 may be oriented substantially orthogonally to illumination window 164. In other embodiments, sensor window 168 and illumination window 164 are one and the same, whereby light source 112 illuminates the test chamber 108 and optical sensor 116 detects illumination from the test chamber 108 through the same window 164, 168.

FIG. 3B shows an embodiment of device 100 including multiple light sources 112, where each light source 112 is oriented to direct optical radiation towards test chamber 108 from a different side of test chamber 108. For example, light sources 112 may direct light into test chamber 108 through opposing test chamber walls 156. The provision of multiple light sources 112 which illuminate test chamber 108 from different directions can provide greater total illumination, allow the use of smaller less expensive light sources 112, reduce the probability that portions of the test mixture 154 are occluded from the optical radiation emitted by light sources 112, and provide more uniform exposure of the test mixture volume to the light emission. As shown, optical sensor 116 can be oriented at a (non-zero) angle to light sources 112. For example, optical sensor 116 may be oriented substantially perpendicularly to light sources 112 as exemplified.

Some or all of test chamber walls 156, except for illumination and sensor windows 164 and 168 or except for windows 164, 168 and pierceable membrane wall 140, may be partially or completely opaque. For example, all of test chamber walls 156 except illumination and sensor windows 164 and 168 or except for windows 164, 168, and pierceable membrane wall 140, may be opaque to all wavelengths of optical radiation, all (human) visible wavelengths of optical radiation, or all wavelengths of optical radiation employed by the test protocol (e.g. the input first wavelength(s), and the output second wavelength(s)). In other embodiments, test chamber walls 156 may be substantially transparent (e.g. transparent according to the basic properties of the selected material, such as transparent plastic or transparent glass, without any treatment or filtering applied for the purpose of limiting or altering transparency), or may be substantially transparent to all wavelengths of optical radiation employed by the test protocol (e.g. the input first wavelength(s), and the output second wavelength(s)).

Test chamber 108 may be permanently connected to portable device 100 as shown in FIG. 1. In this case, portable device 100 may be a disposable device, usable only as many times as there are test chambers 108. Alternatively, test chamber 108 may be included in a cartridge 132 as shown in FIGS. 2-3, which is removably receivable in a reception cavity 144 of device body 104. This allows cartridge 132 to be removed from portable device 100, disposed, and a new cartridge 132 inserted into reception cavity 144 for a subsequent test. In this case, portable device 100 may be operable to execute substantially unlimited tests, subject to the lifespan of other device components (e.g. light source 112, optical sensor 116, and battery 122). Similar to test chamber 108, each of these other device components may be permanently installed in body 104 and non-removable, or may be removable for replacement as required.

Figure 4:
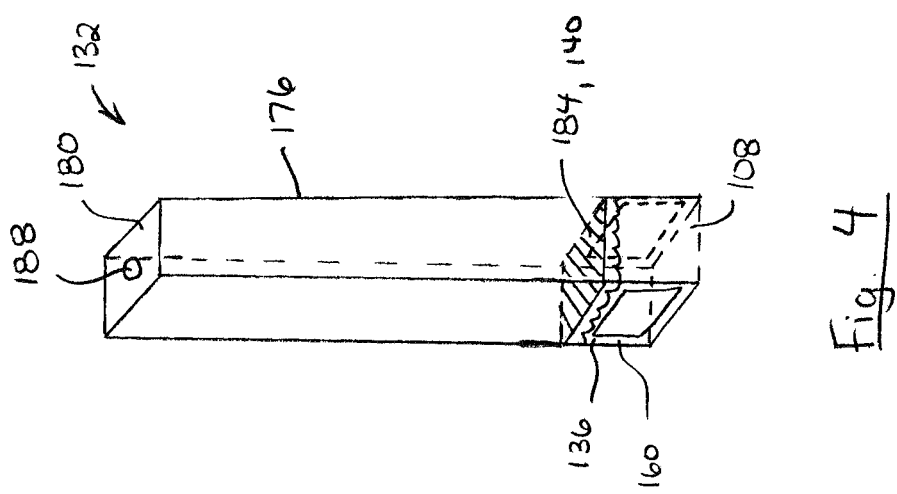
FIG. 4 is a perspective view of the cartridge of FIG. 3.

Referring to FIGS. 1 and 4, in some embodiments cartridge 132 or body 104 may include an inlet passage 176. The inlet passage 176 may provide storage for probe 120, help block ambient light from entering test chamber 108, or both. As shown, inlet passage 176 includes an upstream end 180 and a downstream end 184. Upstream end 180 includes a probe opening 188 for passage of at least a portion of probe 120. Downstream end 184 includes pierceable membrane wall 140 of test chamber 108. Inlet passage 176 can have any size and shape. For example, inlet passage 176 can be cuboid as shown, or have any other regular or irregular shape. Further, inlet passage 176 can be larger (by volume, or in one or more dimensions) than test chamber 108 as shown, or can be equal in size or smaller than test chamber 108.

Figure 4B:
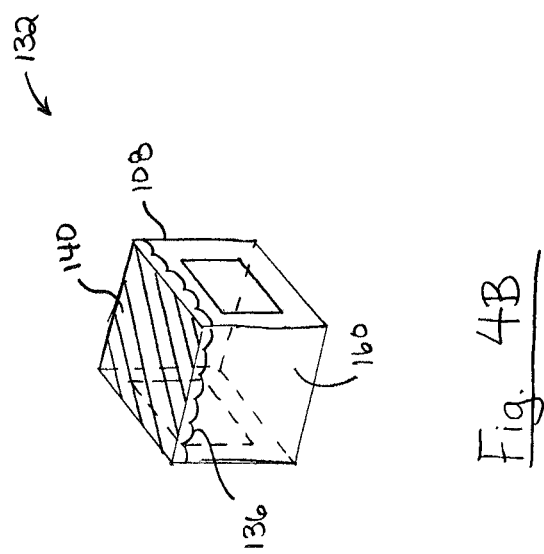
FIG. 4B is a perspective view of a cartridge, in accordance with another embodiment.

Referring to FIG. 4B, in some embodiments cartridge 132 does not have an inlet passage 176. For example, cartridge 132 may comprise test chamber 108 having an externally exposed membrane wall 140 for piercing by a probe to deposit a sample into test chamber interior volume 160 to mix with the analytical reagent of test solution 136 (see FIGS. 3C-3D). This can allow for a smaller cartridge 132 and reception cavity, which can enhance the portability of the portable device.

Figure 4C:
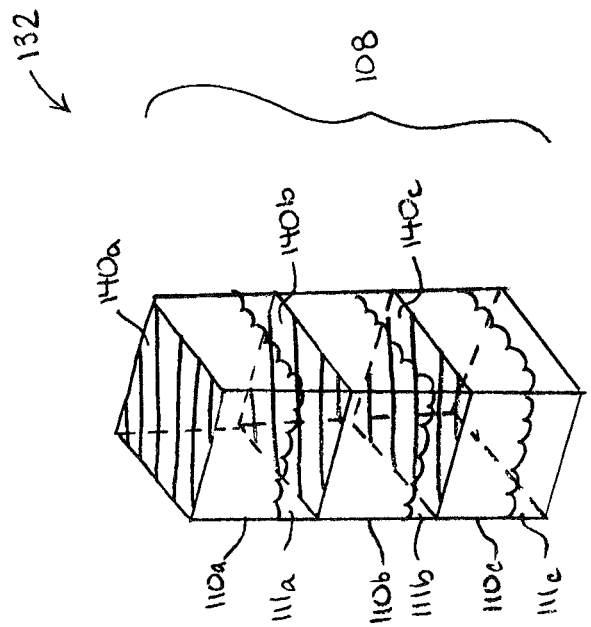
FIG. 4C is a perspective view of a cartridge, in accordance with another embodiment.

Referring to FIG. 4C, in some embodiment cartridge 132 including a test chamber 108 having two or more sub-chambers 110 divided by pierceable membrane walls 140. In the illustrated example, test chamber 108 includes three sub-chambers 110 and the upper end of each sub-chamber 110 includes a pierceable membrane wall 140. As shown, sub-chambers 110 may be arranged sequentially so that a probe can pierce the membrane wall 140 of all of the sub-chambers 110 in a single motion. Each sub-chamber 110 may include sub-chamber contents 111. The contents of two or more of the sub-chambers 110 may collectively form a test solution. For example, the contents 111 of the plurality of sub-chambers 111 may mix together (e.g. in the lowest sub-chamber 110c) upon piercing the membrane walls 140 with a probe. The mixture of contents 111a, 111b, and 111c may form a test solution.

The contents 111 of different sub-chambers 110 may be different. In some embodiments, two or more sub-chamber contents 111 may include one or more different analytical reagents. For example, contents 111a may include one or more first analytical reagents, and contents 111b may include one or more second analytical reagents. In some embodiments, one or more of sub-chamber contents 111 may include an extraction solution which makes the target analyte more available to the analytical reagent in the test mixture. For example, the extraction solution may act to break away bonds or break down fats attached to or encasing a target analyte in a food sample so that the analytical reagent has better access to react with the target analyte. In some embodiments, one or more sub-chamber contents 111 may include a protection solution that is formulated to bind with unwanted molecules so that these unwanted molecules do not react with the analytical reagent in place of the analyte.

In some embodiments, the components of the analytical reagent may be divided between two or more sub-chamber contents 111. For example, one sub-chamber contents 111 may include a dehydrated analytical reagent, and another sub-chamber contents 111 may include hydration (e.g. water), so that when the two sub-chamber contents 111 mix they can form a complete analytical reagent. In some cases, this may help improve the shelf-life of the cartridge 132.

Referring to FIG. 4, test chamber 108 can contain any liquid analytical reagent in liquid test solution 136 suitable for testing for the presence of an analyte indicative of an organic molecular substance (e.g. allergen). For example, the analytical reagent 136 may include one or more compounds that reacts with (e.g. binds to) a target analyte (e.g. *Arachis hypogaea* 1 indicative of a peanut allergen) and thereby produces a change in an optical, magnetic, and/or electrical characteristic. In some examples, the optical, magnetic, and/or electrical characteristic may be excited by an excitation source, which may expose the test mixture to, e.g. optical radiation or a magnetic field. For example, the test mixture may manifest an optically detectable change which may be an increase or decrease of fluorescence. In this case, the test mixture 154 (FIG. 3) will emit, reduce emission, or cease emitting optical radiation of one or more second wavelengths upon illumination by optical radiation of one or more first wavelengths different from the second wavelengths. Depending on the characteristics of the binding reaction and of the fluorescence thereby produced, the one or more second wavelengths may be greater than the one or more first wavelengths because the emitted optical radiation has lesser energy than the illumination optical radiation. In some embodiments, the detectable change may include a temporal pattern of optical, magnetic, or electrical characteristics. For example, the optically detectable change may include an initial emission of at one or more second wavelengths followed by a subsequent emission at one or more third wavelengths. This may be indicative of a cascading or sequential reactions occurring in the test mixture, and this may be indicative of the presence of the analyte.

Preferably, test chamber 108 has a very small internal volume 160, and contains a very small volume of analytical reagent containing test solution 136 accordingly. This helps to promote the portability of portable device 100. It will be appreciated that portable device 100 is capable of detecting clinically significant or lower concentrations of an analyte (i.e. concentrations significant enough to indicate the presence of sufficient allergen to cause a reaction in a human with an allergy, sometimes referred to as LOAEL or lowest observed adverse effect level) in part because the testing (e.g. optical illumination and detection, magnetic field generation and magnetic characteristic detection, and/or electrical characteristic detection) is performed on the test mixture 154 (FIG. 3) in the test chamber 108 instead of downstream (e.g. such as on a test strip). What specifically constitutes a clinically significant concentration depends on the relationship between the analyte and the target organic molecule (e.g. allergen), and the particular target organic molecule (e.g. peanut allergen vs. shellfish allergen). In some examples, test chamber 108 contains less than about 250 µL of test solution, such as 1 µL to 250 µL of test solution. The test chamber interior volume 160 has greater volume than the volume of analytical reagent, and may be less than 1 mL in volume such as 1 µL to 1 mL.

Referring to FIG. 5, the small liquid volume of test solution 136 and the small size of test chamber interior volume 160 may permit portable device body 104 or a cartridge 132 to contain a plurality of test chambers 108 and yet retain the portability of portable device 100. In some examples, device body 104 or a cartridge 132 may include between 2 and 150 test chambers 108. In the illustrated example, portable device 100 includes four test chambers 108, which may be integrated with body 104 or removable as part of a cartridge 132. As shown, test chambers 108 may be movable relative to portable device 100 to align a proceeding test chamber 108b with light source 112 and optical sensor 116 after the preceding test chamber 108a has been used. Alternatively, light source 112 and optical sensor 116 may be movable relative to test chambers 108 or otherwise selectively directable towards the proceeding test chamber 108b after the preceding test chamber 108a has been used.

Figure 5B:
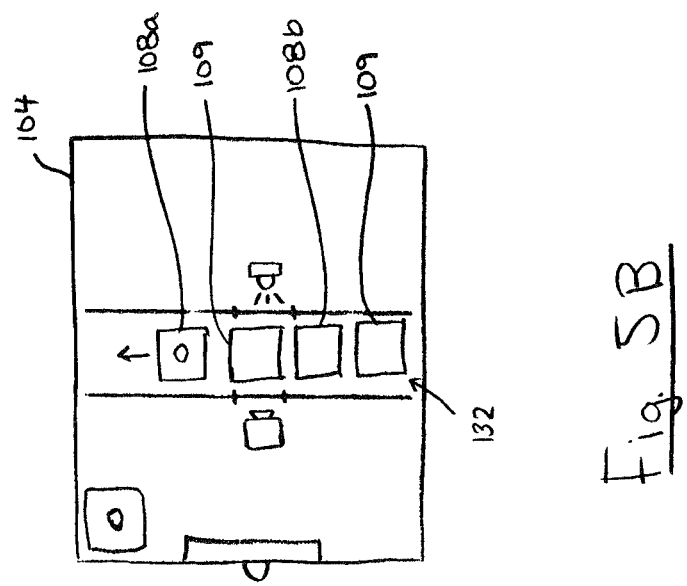
FIG. 5B is a schematic of a portable device including a plurality of test chambers and cleaning chambers.

In some embodiments, portable device 100 may include a plurality of probes 120. For example, portable device 100 may include a probe 120 for each of test chambers 108 in the body 104 or cartridge 132. As exemplified in FIG. 4, an inlet passage 176 may be connected to each of test chambers 108 for storage of a respective probe 120. This allows probes 120 to be single-use and disposable to minimize contamination between tests. Referring to FIG. 5B, in some embodiments portable device 100 may include fewer probes 120 than the number of test chambers 108 in body 104 or cartridge 132. For example, handheld 100 may include just one reusable probe 120. As shown, body 104 or cartridge 132 may include a plurality of test chambers 108 and a plurality of cleaning chambers 109, which may be arranged in alternating sequence as shown. The cleaning chambers 109 may be similar to test chambers 108 except that they may contain a cleaning solution (e.g. isopropyl alcohol and water). In use, the user may use probe 120 to sample and test using a first test chamber 108a. Afterwards, the user may pierce cleaning chamber 109 to contact the probe 120 with the cleaning solution inside to sanitize the probe 120 of contaminants before conducting a subsequent test with the same probe 120. A reusable probe 120 allows for a more compact multi-use portable device 100.

Figure 5C:
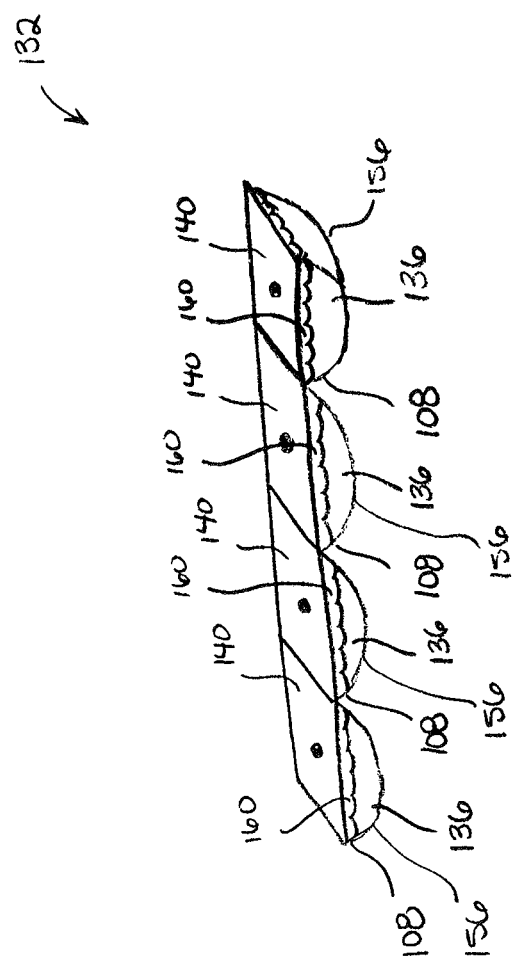
FIG. 5C is a perspective view of a cartridge including a plurality of test chambers.

FIG. 5C shows an example of a cartridge 132 including a plurality of test chambers 108. As shown, each test chamber 108 may include chambers walls 156 and a pierceable membrane wall 140 which define a chamber internal volume 160 containing test solution 136. FIG. 5D shows an example of a cartridge 132 including a plurality of test chambers 108 and a plurality of cleaning chambers 109. As shown, test chambers 108 may be positioned sequentially alternating with cleaning chambers 109. Each cleaning chamber 109 includes chambers walls 156 and a pierceable membrane wall 140 which define a chamber internal volume 160 containing cleaning solution 137.

Figure 4D:
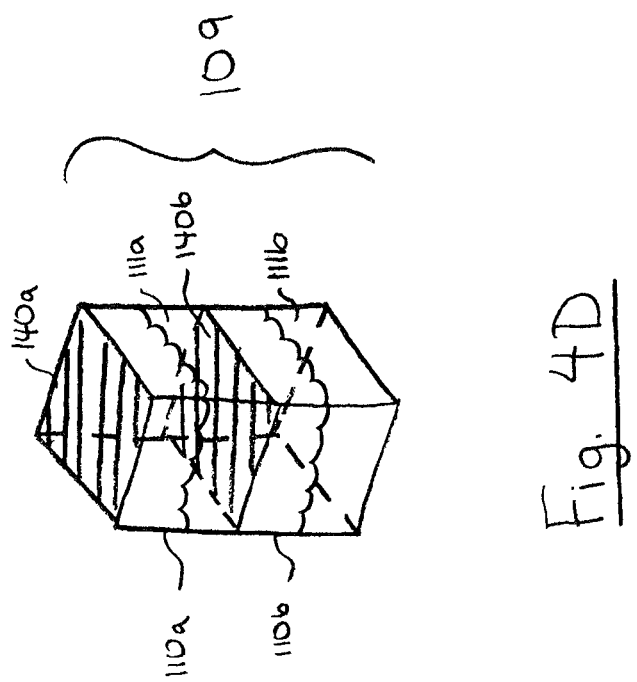
FIG. 4D is a perspective view of a cleaning chamber, in accordance with another embodiment.

Referring to FIG. 4D, in some embodiments, a cleaning chamber 109 may have two or more sub-chambers 110 divided by pierceable membrane walls 140. In the illustrated example, cleaning chamber 109 includes three sub-chambers 110 and the upper end of each sub-chamber 110 includes a pierceable membrane wall 140. As shown, sub-chambers 110 may be arranged sequentially so that a probe can pierce the membrane wall 140 of all of the sub-chambers 110 in a single motion. Each sub-chamber 110 may include sub-chamber contents 111. The contents 111 of two or more of the sub-chambers 110 may collectively form a cleaning solution. For example, contents 111a may include water, and contents 111b may include isopropyl alcohol, which mix upon piercing by a probe to form a cleaning solution.

Referring to FIG. 3, light source 112 can be any device suitable for emitting optical radiation having one or more first wavelengths at sufficient intensity as required by the test protocol. For example, light source 112 may include an LED light, an incandescent light, a halogen light, a fluorescent light, a laser light, or combinations thereof, which has been configured to emit optical radiation having at least the one or more first wavelengths required by the test protocol. In some cases, light source 112 may additionally emit extraneous optical radiation having one or more wavelengths other than those required by the test protocol. If this extraneous optical radiation is unwanted (e.g. would negatively impact the quality of the test), then illumination window 164 may include a filter 172 to block the extraneous optical radiation while allowing the optical radiation having the one or more first wavelengths to pass.

Optical sensor 116 can be any device suitable for detecting optical radiation having one or more second wavelengths with sufficient sensitivity as required by the test protocol. In some cases, optical sensor 116 may additional detect extraneous optical radiation having one or more wavelengths other than those required by the test protocol. If detecting this extraneous optical radiation is unwanted (e.g. would negatively impact the quality of the test), then sensor window 168 may include an optical filter 189 to block the extraneous optical radiation while allowing the optical radiation having the one or more second wavelengths to pass. In other embodiments, optical filter 189 may be formed in body 104 between optical sensor 116 and test chamber 108. For example, a portion of reception cavity 144 may include optical filter 189 instead of or in addition to sensor window 168.

Display 128 can be any device suitable for producing a visual indication of the results of the test. For example, display 128 may include a light (e.g. LED, incandescent, halogen, etc.), an LCD screen, an LED screen, an e-ink display, an OLED display, or combinations thereof. Display 128 may be a touchscreen display to allow user interactivity (e.g. menu or feature selection) or a non-touchscreen display. In the illustrated example, display 128 includes two LEDs 190 that are selectively illuminable (e.g. by processor 124) to communicate whether or not an analyte (or a threshold concentration of an analyte) indicative of a target organic substance (e.g. allergen) was found in the food sample. In other embodiments, display 128 may communicate other information, such as the identity of the analyte detected, the identity of the target organic substance associated with the detected analyte, and the concentration of that analyte in the sample. In some embodiments, portable device 100 does not include a display 128. For example, portable device 100 may communicate wirelessly, or by wire, to another device (e.g. smartphone) which may present the results of the test.

Referring now to FIG. 2, probe 120 may be any device suitable for piercing food to collect food samples, and for piercing a test chamber membrane wall 140 to deposit collected food samples into a volume of liquid test solution 136 containing analytical reagent. In the illustrated embodiment, probe 120 includes an elongate probe shaft 192 having a distal end 196 and a proximal end 200. As shown, probe shaft distal end 196 may be pointed for piercing food to collect food samples, and for piercing test chamber membrane wall 140 to deposit collected food samples. Optionally, probe 120 may further include a handle 204 connected to probe shaft proximal end 200 to provide a manual gripping surface for the user.

Probe shaft 192 may be formed of any material(s) suitable for piercing food, collecting food samples from pierced food, and piercing test chamber membrane wall 140. Preferably, probe shaft 192 is sufficiently rigid so as not to buckle when piercing food and test chamber membrane wall 140. For example, probe shaft 192 may be formed of wood, metal, plastic, ceramic, or glass. Portable device 100 may include or be compatible with a plurality of different probes 120, which may be selected based on the food to be sampled. For example, a probe having a probe shaft 192 including a porous material (e.g. wood) may be well suited to testing liquids and liquid containing foods.

Probe shaft 192 (or a portion thereof) may include one or more surface features to promote capture or sampling of food samples from various types of food. The surface features may be naturally provided by the material, or may be imparted by physical or chemical means. Referring to FIG. 6, in some embodiments, at least a portion of probe shaft 192 may be pitted with a plurality of pits 208. Pits 208 may derive from the substrate material, or may be imparted by chemical treatment (e.g. by acid treatment) or physical treatment (e.g. by laser dimpling). Pits 208 may have any size suitable for promoting food samples to collect on probe shaft 192. For example, pits 208 may have a largest dimension 212 of 25 μm to 250 μm, and probe shaft 192 may include 10 or more pits 208 (e.g. 10-5000 pits 208). In use, pit edges 216 may act abrasively on the pierced food to dislodge food samples, and small food samples may collect inside pits 208.

Figure 6B:
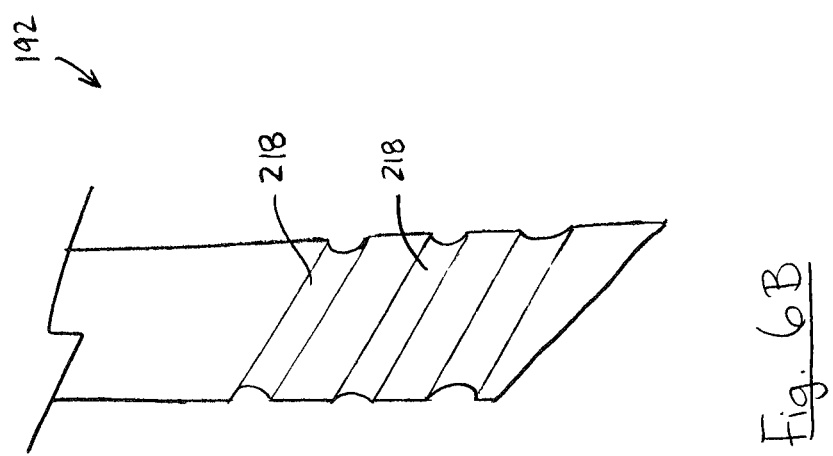
FIG. 6B is a side elevation view of a portion of a probe shaft including surface channels.

Turning to FIG. 6B, in some embodiments probe shaft 192 may include one or more surface channels 218. Surface channels 218 may be formed as elongated concavities which extend along the surface of probe shaft 192. In the illustrated example, surface channels 218 extend in a helical pattern around probe shaft 192. FIG. 6C shows an example including a plurality of surface channels 218 which are discontinuously spaced apart along a helical path around probe shaft 192.

Referring to FIG. 3, due to the small volume of test chamber 108 and the small volume of test solution 136 inside, large food samples 220 should be prevented from entering test chamber 108 where those food samples 220 might interfere with the test (e.g. by overwhelming the analytical reagent, blocking the field of view of optical sensor 116, or block optical radiation from light source 112). Membrane wall 140 may act as a mechanical filter to prevent entry of large samples 220 into test chamber 108. When probe shaft 192 penetrates test chamber membrane wall 140, the membrane wall 140 may act to wipe along probe shaft 192 thereby preventing entry of large food samples 220 into test chamber 108. However, small particles contained in, e.g. pits 208 (FIG. 6) may be allowed to pass. Accordingly, the size and number of pits 208 may help to regulate the size and quantity of food samples deposited into test chamber 108.

Referring to FIG. 7, in some embodiments, probe shaft distal end 196 may include a cavity (i.e. concave portion) 224. As shown, the cavity 224 may be centrally positioned and bordered by a periphery 228 of shaft distal end 196. Similar to pits 208 (FIG. 6), cavity 224 may provide a recess where food samples 152 (FIG. 3) can collect during food sampling, and which may not be dislodged during piercing of membrane wall 140. Cavity 224 may have any depth 232 suitable for collecting small food samples 152 (FIG. 3). For example, cavity depth 232 may be between 25 μm and 2500 μm.

Referring to FIG. 8, in some embodiments, at least a portion of probe shaft 192 may include abrasive protrusions 236. Abrasive protrusions 236 may help to break or chip away small food samples 152 (FIG. 3) from hard foods, such as nuts. The abrasive protrusions 236 may also help to grip food samples 152 (FIG. 3) onto probe shaft 192 so that small food samples 152 (FIG. 3) resist being dislodged upon piercing membrane wall 140. Abrasive protrusions 236 can have any protrusion height 240 suitable for breaking away small food samples 152 (FIG. 3) from hard foods and/or gripping onto food samples 152. For example, protrusion height 240 may be between 25 μm and 250 μm, and probe shaft 192 may have 10 or more protrusions 236 (e.g. 10 to 5000 protrusions 236). Protrusions 236 may be derived from the substrate material naturally, or may be applied to probe shaft 192, such as by spraying probe shaft 192 with a rough coating of particulates.

FIGS. 6-8 illustrate various examples of probe shaft surface features. It will be appreciated that in some embodiments, these features may be combined. For example, a probe shaft 192 may include one or more (or all) of the features described above (e.g. porosity, pitted surface, distal end cavity, and abrasive protrusions).

Upon piercing test chamber 108, at least a portion of probe shaft 192 is submerged in or at least makes contact with test solution 136, whereby food samples collected in or on probe shaft 192 may be released into test mixture 154. In some embodiments, agitation may promote food samples to be dislodged from probe shaft 192 into the test solution 136, and may accelerate the reaction between the test solution 136 and the analyte in the food sample (if that analyte is present). Referring to FIG. 3, agitation may be achieve by shaking portable device 100 (e.g. while probe shaft penetrates membrane wall 140), or by shaking probe 120 (e.g. repetitiously moving probe 120 inwardly and outwardly from test chamber 108). Alternatively or in addition, portable device 100 may include an agitator or vibrator 280 that is operable to vibrate test chamber 108 or apparatus 100 as a whole.

Still referring to FIG. 3, depending on the test protocol, it may be necessary to prevent contaminants, such as light, air, magnetism, heat, and humidity from entering test chamber 108 before testing, during testing, or while sensing. This may be the case where, for example, optical radiation employed by the test protocol (e.g. optical radiation having the input first wavelength(s) or the output second wavelength(s)) is normally found in ambient light (e.g. sunlight, or convention indoor lighting). In the illustrated example, inlet passage 176 includes a narrow probe opening 188 sized to accommodate probe shaft 192, whereby probe shaft 192 may substantially reduce or inhibit one or more (or all of) light, air, heat, and humidity from entering test chamber 108 through the probe opening 188. Alternatively, or in addition to a narrow probe opening 188, probe 120 may include a flange 244 at probe shaft proximal end 200, which is sized to cover at least probe opening 188. As shown, probe flange 244 may form part of probe handle 204 (if present) or may be a discrete component from probe handle 204. Probe flange 244 may form a seal with body 104 and/or cartridge 132. For example, probe flange 244, body 104, and/or cartridge 132 may include one or more seals 246 that engage with probe flange 244 to substantially reduce or inhibit passage of one or more (or all) of light, air, magnetism, heat, and humidity into reception cavity 144 and/or test chamber 108. In some embodiments, at least a portion of body 104 is sealed against entry of one or more (or all) of light, air, magnetism, heat, and/or humidity.

Figure 10:
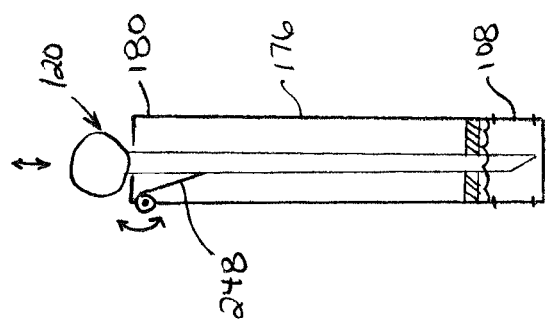
FIGS. 9 and 10 are cross-sectional views of an inlet passageway, test chamber, and probe where the inlet passageway has a door.
Figure 9:
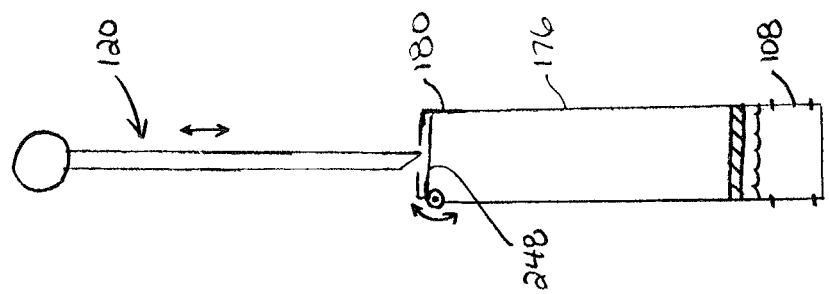

FIGS. 9 and 10 show an example of inlet passage 176 include a door 248. As shown, inlet passage door 248 has a closed position (FIG. 9) in which door 248 blocks entry of ambient light into test chamber 108, and an open position (FIG. 10) in which door 248 admits entry of probe 120 into test chamber 108. Inlet passage door 248 allows testing to be performed with probe 120 removed from test chamber 108, so that probe 120 does not interfere with the test (e.g. block the field of view of the optical sensor). It will be appreciated that door 248 may be positioned anywhere along inlet passage 176, such as at upstream end 180 as shown. Optionally, door 248 may be biased to the closed position (e.g. by a spring) so that door 248 closes automatically upon withdrawing probe 120.

FIGS. 11 and 12 show an example of probe 120 including a retractable probe shaft 192. As shown, probe shaft 192 is movable relative to probe flange 244 between a retracted position (FIG. 11) and an extended position (FIG. 12). This allows probe flange 244 to be seated on inlet passage upstream end 180, and probe shaft 192 reciprocated between the retracted and extended positions to dislodge food samples 152 from probe shaft 192 into the test mixture 154, and agitate the test mixture 154. Further, this allows probe shaft 192 to be extended deeply into test chamber 108 for greater submersion into test solution 136. In the extended position, probe shaft 192 may interfere with the test, such as by obstructing the line of sight of optical sensor 116 or by obstructing the illumination of some portions of test mixture 154 by light source 112. However, in the retracted position, probe shaft 192 may be moved so as not to interfere with the test. In some embodiments, probe shaft 192 may be biased to the retracted position so that probe 120 will not interfere with the test when the user releases probe 120. For example, probe shaft 192 may be biased to the retracted position by a spring 252 or another biasing member.

Figure 13:
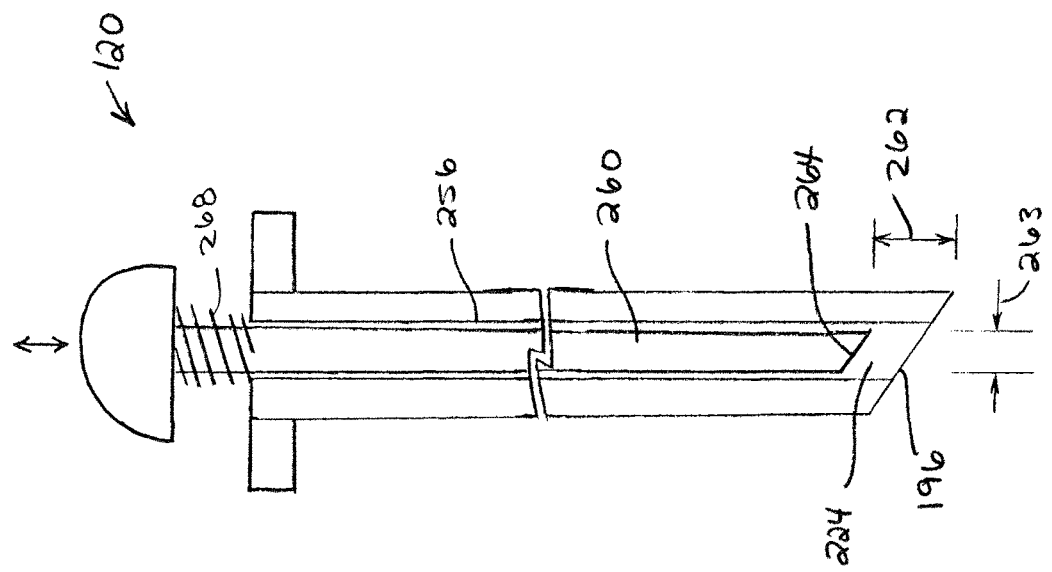
FIGS. 13 and 14 are cross-sectional views of a probe including a shaft having a lumen and a retractable plunger in the lumen.
Figure 14:
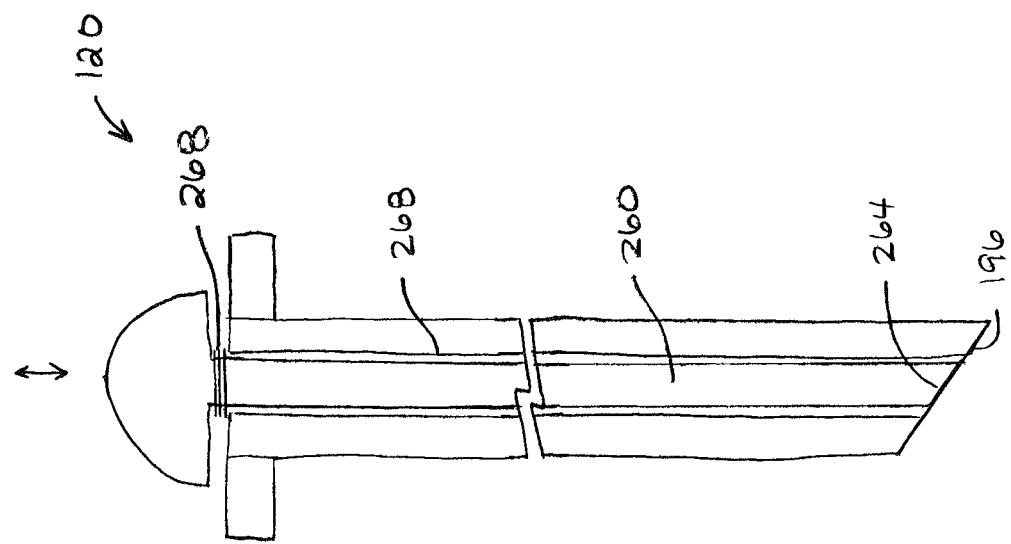

FIGS. 13 and 14 show an example of probe 120 including a lumen 256 and a retractable plunger 260 inside the lumen 256. As shown, plunger 260 is moveable between a retracted position (FIG. 13) and an extended position (FIG. 14). In the retracted position, plunger distal end 264 is retracted from probe shaft distal end 196 thereby forming a cavity 224. As describe above with reference to FIG. 7, food samples may be collected in cavity 224, and the collected food samples may resist being dislodged when piercing membrane wall. In this case, plunger 260 is movable from the retracted position to the extended position to discharge any food samples collected in cavity 224 into the test chamber. Plunger 260 may be retractable by any distance suitable for providing a cavity 224 for small food samples. For example, plunger 260 may be retractable by a distance 262 of between 25 µm and 2500 µm and lumen 256 may have a diameter 263 of between 25 µm and 2500 µm. In some embodiments, plunger 260 may be biased to the retracted position. For example, probe 120 may include a spring 268 or another biasing member that biases plunger 260 to the retracted position.

Figure 15:
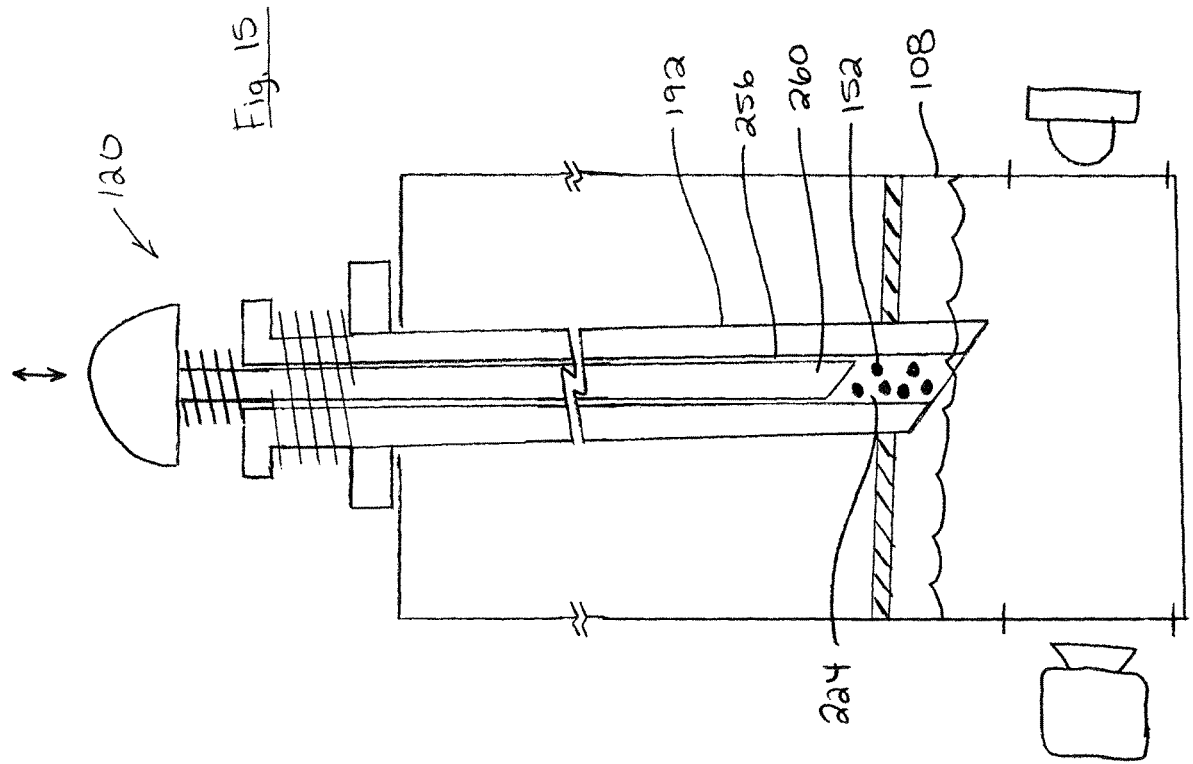
FIGS. 15 and 16 are cross-sectional views of an inlet passageway, test chamber, and probe, where the probe has a retractable shaft, and the shaft includes a lumen and a retractable plunger in the lumen.
Figure 16:
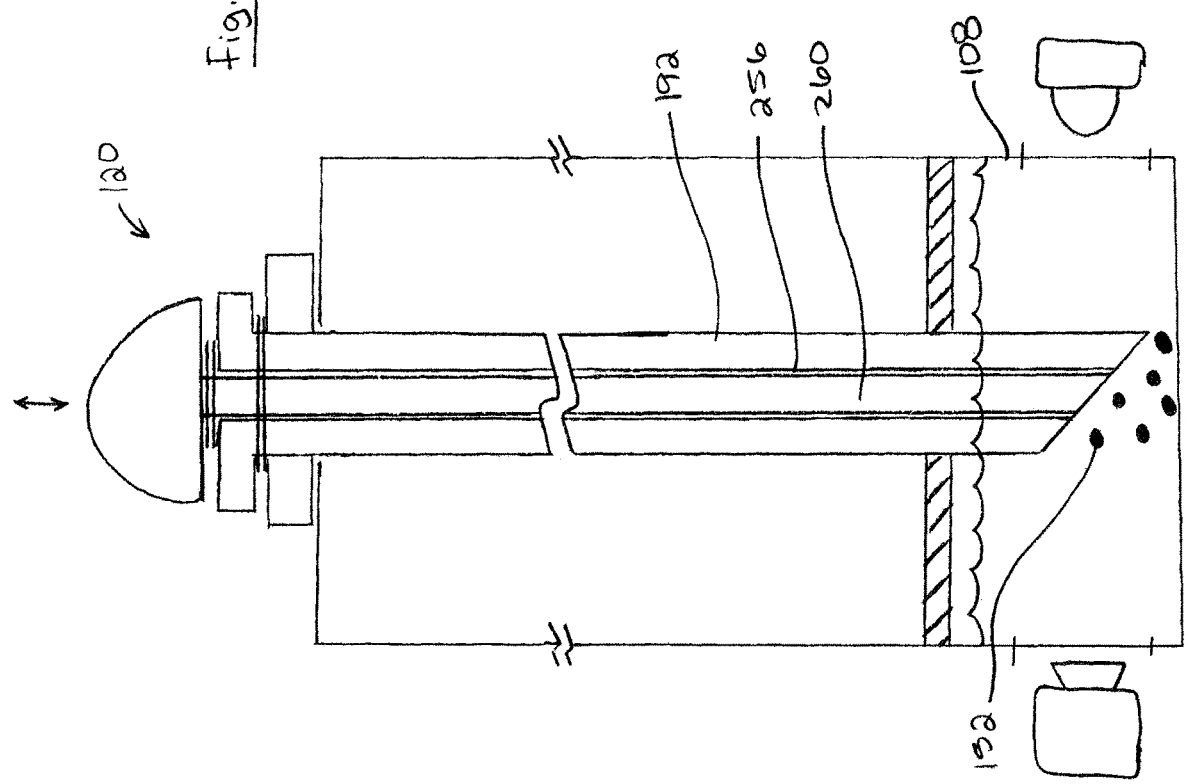
Figure 17:
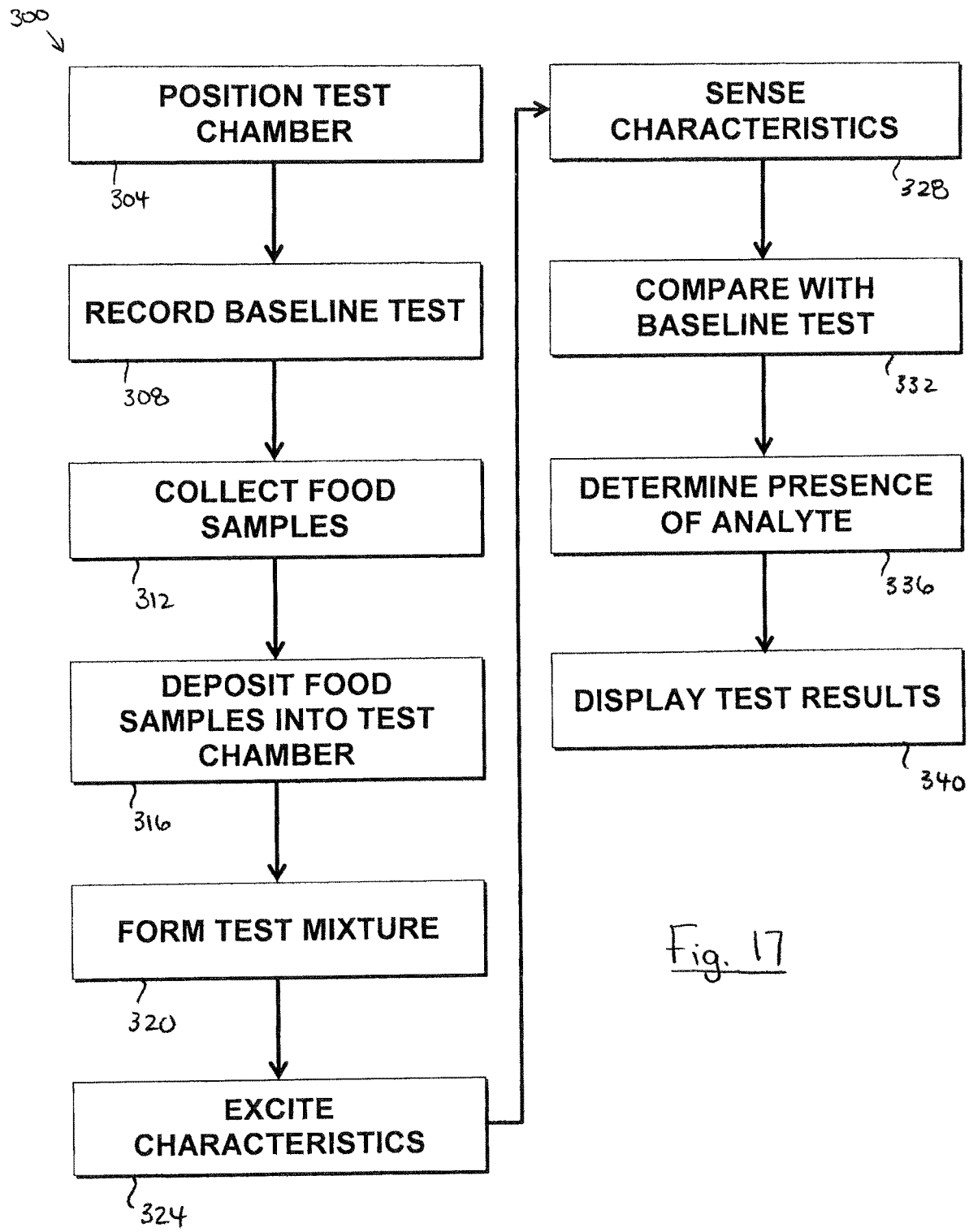
FIG. 17 is a flowchart illustrating a method of detecting an analyte in a substance.

It will be appreciated that probe 120 may include any one or more (or all) of the features of probe 120 described above (e.g. described with reference to FIGS. 6 to 14). For example, FIGS. 16 and 17 show an example of a probe 120 including a retractable probe shaft 192 as describe above with reference to FIGS. 12-13, and a probe shaft 192 with a lumen 256 and a retractable plunger 260 inside the lumen 256 as describe above with reference to FIGS. 14-15. As shown, probe shaft 192 and plunger 260 may be movable between a retracted position (FIG. 15) and an extended position (FIG. 16). In the retracted position, probe shaft 192 may be positioned so as not to interfere with the test, and in the extended position probe shaft 192 may be moved deep within the test chamber 108 and plunger may discharge any food samples 152 contained in cavity 224 into the test chamber 108.

FIG. 17 is a flowchart illustrating a method 300 of detecting an analyte in a substance. It will be appreciated that, in some embodiments, some steps of method 300 may be performed in a different order than shown, may be performed simultaneously where shown sequentially, and may be omitted altogether. Also, in some embodiments, additional steps not shown may be included in method 300.

At 304, a test chamber is inserted into the portable device. For example, referring to FIG. 2, a cartridge 132 containing a test chamber 108 may be inserted into a reception cavity 144 formed in device body 104. Where portable device 100 includes an integral test chamber 108, as in FIG. 1, this step is not performed. Where handheld device 100 includes a plurality of test chambers 108, as in FIG. 5, this step may be substituted by advancing the next test chamber 108b in sequence.

At 308, a baseline test is performed and the results recorded. Referring to FIG. 1, the baseline test may be performed automatically upon user-activation of a user interface element (e.g. button 272) or automatically upon inserting test chamber 108 into device body 104 (FIG. 2). In some embodiments, due to the tiny volume of test solution 136 in the test chamber, the exact volume of test solution 136 from test chamber 108 to test chamber 108 can be prone to relevant variation. Also, in the case of a portable device 100 that utilizes cartridges 132, user handling of the cartridges 132 can potentially affect the test results (e.g. due to fingerprints on the illumination or sensor windows). To account for such potential variability, the test solution 136 in the test chamber 108, free of food samples, may be have its characteristics (e.g. optical, magnetic, and/or electrical) excited by an excitation source, and these characteristics detected by a sensor (e.g. sensor 116, 116b, and/or 116c), in the same manner as will later be performed on the test mixture including the food samples. The results of this baseline test are recorded (e.g. by the processor 124) for later comparison. In alternative embodiments, the baseline test results are sent to an computing device (e.g. smartphone) for storage and later comparison.

In some embodiments, the test protocol does not require a baseline test. For example, the nature of the input and output emissions or the pattern of detected emissions (static or temporally patterned) indicative of the analyte may provide sufficiently consistency that baseline testing is not required. In the case of a portable device 100 including a non-removable test chamber, reduced user handling of the test chamber 108 may reduce variability so that the results of any such baseline testing would be predeterminable.

At 312, food samples are collected. Referring to FIG. 2, a user manipulates probe 120 to pierce food 148 with the probe shaft 192. Preferably, the user pierces food 148 several times to collect samples from various portions of food 148. This provides an improved opportunity to detect an analyte that may be present only in certain portions of the food 148.

At 316, the food samples are deposited into the test chamber. Referring to FIG. 3, the user manipulates the probe 120 carrying food samples 152 taken at 312, and pierces test chamber membrane wall 140 thereby inserting at least probe shaft distal end 196 into test chamber 108. The food samples 152 release from probe 120 into test solution 136 by interaction of the test solution 136 with probe shaft 192, by agitation of probe shaft 192 in test chamber 108, by agitation of test solution 136, by operation of vibrator 280, by operation of a probe shaft plunger 260 (FIG. 14), or combinations thereof.

At 320, the test mixture is formed. Referring to FIG. 3, this may include agitating test chamber 108 or test solution 136 to accelerate a reaction with the deposited food samples 152. In some cases, this step overlaps with depositing food samples 152 into the test chamber 108. For example, agitation performed to deposit the food samples 152 may be sufficient to form the test mixture 154. In some embodiments, the test mixture 154 is formed substantially instantaneously upon contact between the food samples 152 and the test solution 136 so that no additional user action is required to form the test mixture 154 once the food samples 152 are deposited.

At 324, the characteristics of the test mixture in the test chamber is excited (e.g. illuminated by the light source, or exposed to a magnetic field). Referring to FIGS. 1, and 3C, the excitation source (e.g. light source 112, or magnetic field source 112*b*) may activate upon user-activation of a user interface element (e.g. button 276) or automatically upon inserting or withdrawing probe 120 from portable device 100. The excitation source 112, and/or 112*b* exposes the test chamber 108 to optical radiation, or a magnetic field to excite optical, magnetic, or electrical characteristics of the test mixture 154.

At 328, a sensor detects characteristics of the test mixture. Referring to FIGS. 1, 3C, and 3D, the optical sensor 116, magnetic field detector 116*b*, and/or electrical sensor 116*c* detects optical, magnetic, and/or electrical characteristics according to the test protocol. The detection at 328 may overlap with the excitation at 324, or begin after the excitation at 324 has ceased. In the embodiment of FIG. 3D, detection at 328 may occur absent any excitation at 324. A readout from the sensor 116, 116*b*, and/or 116*c* is sent to the processor 124 or an computing device (e.g. smartphone) for analysis.

At 332, the readout recited at 328 is compared with the earlier baseline test to determine the delta. Referring to FIGS. 1, 3C, and 3D, the processor 124 may determine the difference in optical, magnetic, or electrical characteristics (e.g. light intensities or wavelengths) between the readout and the earlier baseline results. The delta may take the form of one or more static values, and/or temporally patterned values. Where the test protocol does not include a baseline test, this step is not performed. In some embodiments, the readout of the sensor(s) is sent to an computing device (e.g. smartphone) for comparison with the baseline results.

At 336, the presence of an analyte associated with a target organic molecule (e.g. allergen) is determined. Referring to FIGS. 1, 3C, and 3D, the processor 124 assesses the delta determined at 332 and/or the test mixture readout from sensor 116, 116*b*, and/or 116*c* at 328 to determine whether the sample contains the analyte (or a relevant quantity thereof). For example, the processor 124 may determine that the analyte is present in the sample if the change in the detected characteristics (e.g. light intensity at one or more optical radiation wavelengths) exceeds or falls below a threshold intensity, or varied in according to a predetermined pattern across a period of time (a "temporal pattern"). In some embodiments, determining the presence of the analyte is performed on a remote device (e.g. smartphone).

At 340, the test results are displayed. Referring to FIG. 1, the processor 124 may control display 128 to provide a visual indication of whether the analyte (or a relevant quantity thereof) was detected in the food sample.

Figure 18:
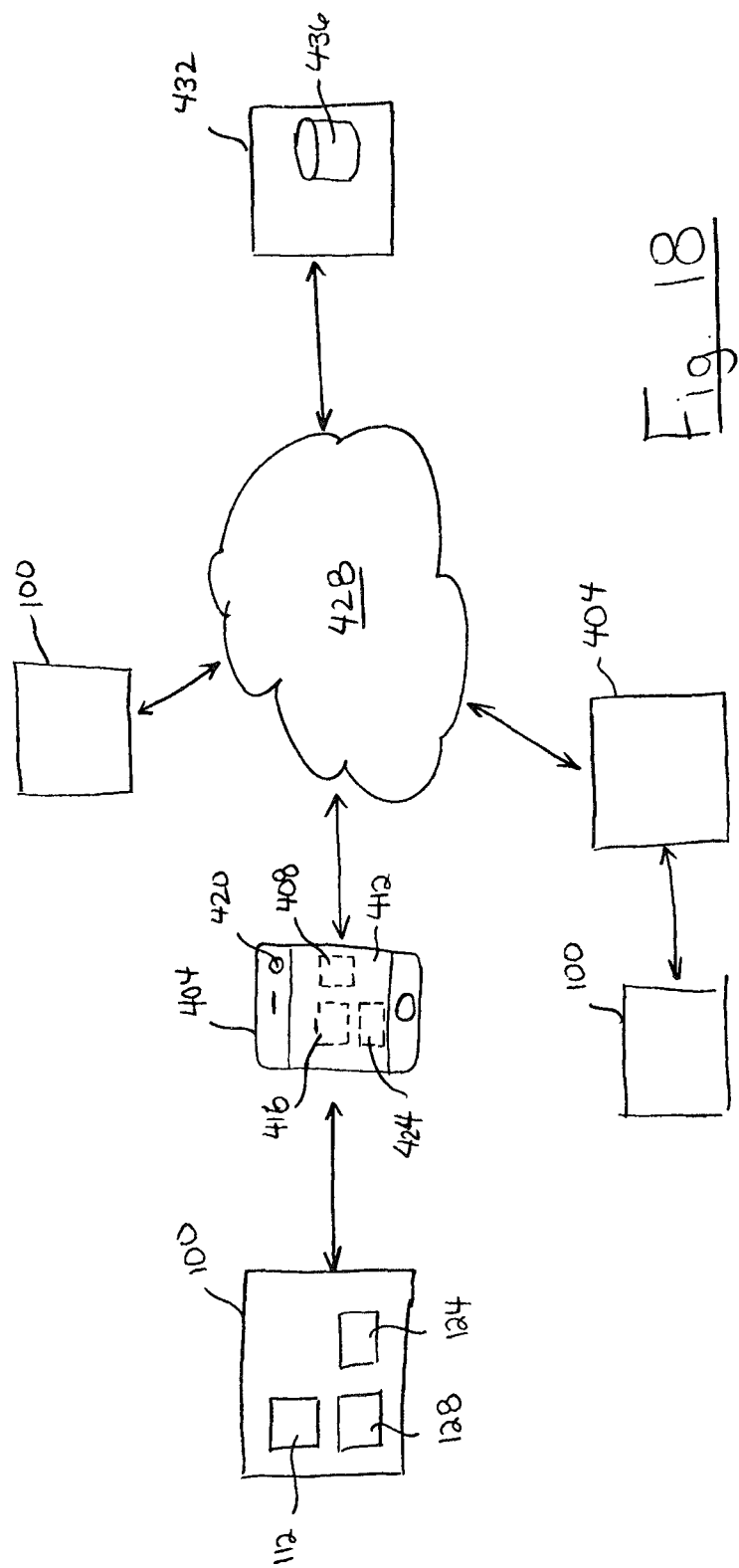
FIG. 18 is a schematic illustrating a portable device connected to a network via an computing device.

Reference is now made to FIG. 18. In some embodiments, portable device 100 may be part of an organic molecular sensing system 1802. In system 1802, portable device 100 is coupled to an external computing device 404 to allow data communication between the portable device 100 and the computing device 404. The computing device 404 may be any device capable of receiving data from portable device 100, such as a smartphone, tablet computer, laptop, desktop, embedded computing devices, wearable devices or server computer. Portable device 100 may communicate with computing device 404 in any means that allow the transmission of data between portable device 100 and computing device 404, such as by wired connections (e.g. USB cable) or wireless connections (e.g. Bluetooth, WiFi).

In some embodiments, portable device 100 sends computing device 404 sensor data from sensor 112. This can allow computing device processor 408 to interpret the sensor data to assess whether an analyte is present in the test mixture. The computing device 404 may include a display 412 to present the results to the user, or the computing device 404 may transmit the results back to the portable device 100 for display on portable device display 128. For example, the portable device 100 may transmit sensor data to a smartphone, tablet, computer or other computing device. Software operating on the computing device may interpret the data and provide results to a user on a display. The software may be an application, web application or other executable software. Alternatively, portable device 100 may send computing device 404 test results computed by portable device processor 124 (i.e. the assessment of whether an analyte is present in the test mixture).

Software executing on the portable device 100 or the computing device 404 (e.g. a smartphone application, web application, embedded software) may collect data to associate with the test results. For example, at least one of the portable device 100 and the computing device 404 may associate location information with the test results. The location information may be determined using a GPS unit 416 internal to or connected to one or both of the portable device 100 and computing device 404, may be determined using communication network protocols (e.g. cellular tower information, gateway address, or IP address), or may be received from user input (e.g. in a location entry field in a data entry page or form or in response to prompt).

In some embodiments, the portable device 100 or the computing device 404 may associate contextual information with the test results. For example, contextual information may include food information including a name for the sample food product (such as the name of the food product on a restaurant menu), an image of the food product (which may be captured by a camera 420 internal to or connected to one or both of the portable device 100 and computing device 404 or obtained from another source such as an image from a restaurant website or menu), and other information, comments or notes provided by the user information.

One or both of portable device 100 and computing device 404 may store the test results and associated information (e.g. location and substance information) in a storage device 424 internal to or connected to one or both of the portable device 100 and computing device 404. In some example, this may allow the user to refer to these results at a later date, such as when visiting the location (e.g. restaurant) of a previous test result, or when using (e.g. eating) a substance (e.g. food) corresponding to substance information of a previous test result. This can allow the user to make informed decisions based on previous test results.

Figure 19:
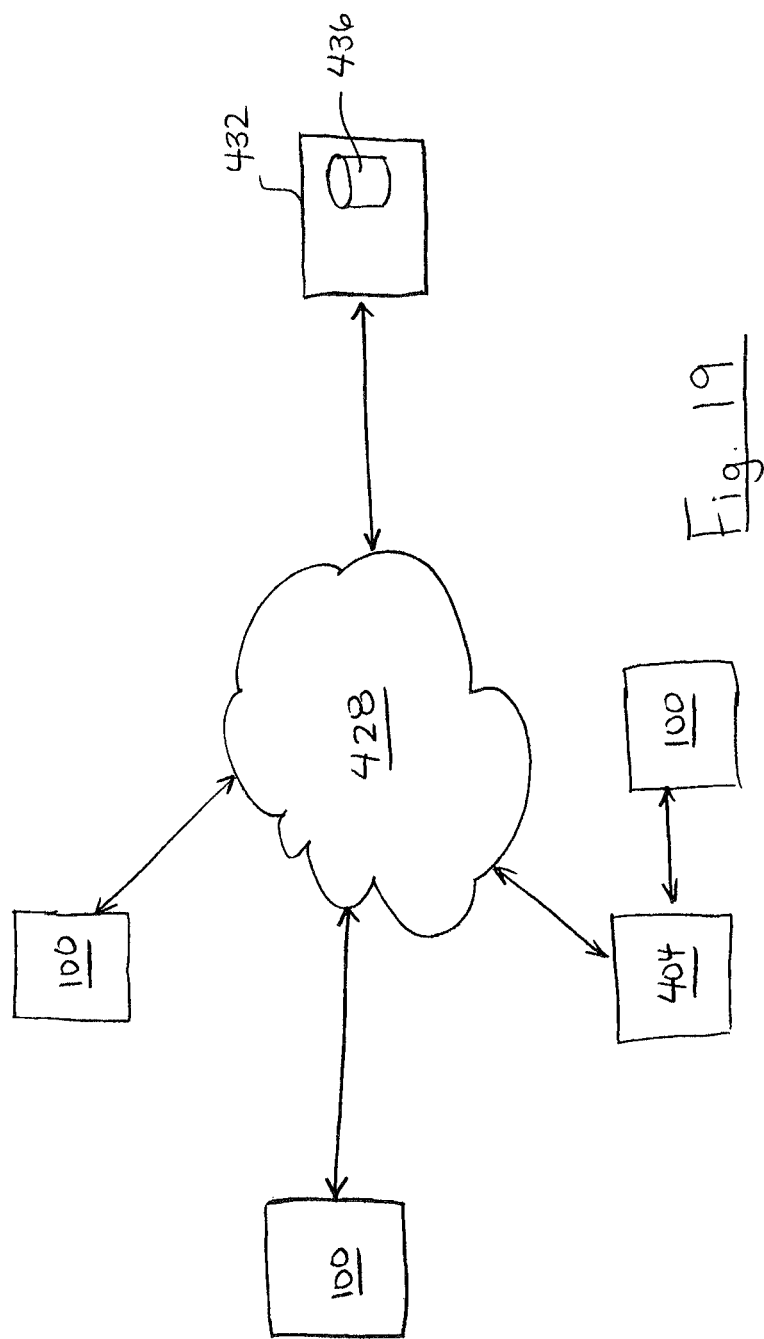
FIG. 19 is a schematic illustrating a portable device connected to a network.

In some embodiments, one or both of the portable device 100 and computing device 404 can communicate across a network 428 such as the internet. FIG. 18 shows an example with computing device 404 connected to network 428. FIG. 19 illustrates a system 1902 which shows an example of portable device 100 connected to network 428. Portable device 100 and computing device 404 can be connected to the network 428 in any manner that allows data transmission to and/or from the network 428. For example, portable device 100 and computing device 404 may be connected to the network 428 by wire (e.g. USB cable) or wirelessly (e.g. Bluetooth, Wifi 802.11, 3G, or LTE).

Alternatively or in addition to local storage of test results (and optionally associated location and contextual information) on portable device 100 or computing device 404, the test results and/or associated information may be communicated across network 428 to a server device 432. The server device 432 may store the test results and/or associated information in a storage device 436 in connection with a user account corresponding to portable device 100 and/or computing device 404, or else anonymously. As shown, server device 432 may receive and store test results and/or associated information from a plurality of connected portable devices 100 and/or computing devices. This can allow the test results and/or associated information to be aggregately stored on server storage device 436. In some examples, portable device 100 and/or computing device 404 may be able to receive information based on the data in server storage device 436. For example, portable device 100 and/or computing device 404 may retrieve from server device 436 test results of substances (e.g. foods) reported by the network of portable devices 100 and/or computing device 404 for a particular location (e.g. restaurant), for a particular menu item. The portable device 100 may retrieve in response to a request form a user or automatically based on the location of the portable device. This can allow a user to make informed decisions about locations to visit and substances to use (e.g. consume) based on the reported test results and/or associated information reported by the user and by other users.

Test results and/or associated information may also be analyzed by an operator of the server device 432 to assess compliance of a restaurant or other facility with food preparation guidelines, such as avoidance of particular ingredients to prepare analytic results. The analytic results may be used, for example, to provide reports to the restaurant regarding the restaurant's performance, to provide reports to users of portable devices 100 regarding food safety at restaurant or to provide reports to regulatory authorities.

Test results, associated information and/or analytic results may be associated with a menu for a location and provide to a user in an automated manner. For example, a user may access a restaurant menu using software operating on a computing device. Items on the menu may be annotated or identified based on previously recorded test results, associated information and analytic results for such items.

While the above description provides examples of the embodiments, it will be appreciated that some features and/or functions of the described embodiments are susceptible to modification without departing from the spirit and principles of operation of the described embodiments. Accordingly, what has been described above has been intended to be illustrative of the invention and non-limiting and it will be understood by persons skilled in the art that other variants and modifications may be made without departing from the scope of the invention as defined in the claims appended hereto. The scope of the claims should not be limited by the preferred embodiments and examples, but should be given the broadest interpretation consistent with the description as a whole.

Items

Item 1: A portable device for detecting an analyte associated with a target organic molecule in a liquid and/or solid substance, the device comprising:
    a test chamber containing a liquid volume of test solution including an analytical reagent selected to react with the analyte, the test chamber sealed by a pierceable membrane wall;
    a probe removably positionable to pierce the membrane wall to deposit a sample in the test chamber to form a test mixture with the test solution; and
    a sensor positioned to detect one or more characteristics of the test mixture in the test chamber indicative of a reaction between the analyte and the analytical reagent.

Item 2: The portable device of item 1, further comprising:
    an excitation source to excite at least one of the characteristics of the test mixture.

Item 3: The portable device of item 2, wherein:
    the excitation source includes at least one of a light source, an electric field source, an electric current source, and a magnetic field source.

Item 4: The portable device of item 1, wherein:
    the one or more characteristics including one of more of magnetic, electrical, and optical characteristics.

Item 5: The portable device of item 1, further comprising:
    a processor communicatively coupled to the sensor to assess whether the sample contains the analyte based at least in part on the detected one or more characteristics.

Item 6: The portable device of item 1, further comprising:
    a display controllable to indicate the presence of the analyte.

Item 7: The portable device of item 1, further comprising:
    a battery electrically connected to the sensor.

Item 8: The portable device of item 2, wherein:
    the test chamber has an illumination window and a sensor window,
    the excitation source comprises a light source directed to illuminate at least a portion of the test chamber through the illumination window, and the sensor comprises an optical sensor directed to detect optical radiation from the test chamber through the sensor window.

Item 9: The portable device of item 1, wherein:
the test chamber contains between 1 μL and 250 μL of the test solution.

Item 10: The portable device of item 1, wherein:
the test chamber has a volume of less than 1 mL.

Item 11: The portable device of item 8, wherein:
the light source emits optical radiation having one or more first wavelengths, and
the optical sensor detects optical radiation having one or more second wavelengths different from the one or more first wavelengths.

Item 12: The portable device of item 11, wherein:
the one or more second wavelengths are greater than the one or more first wavelengths.

Item 13: The portable device of item 1, further comprising:
a body containing the sensor, and a reception cavity, wherein the test chamber is removably positionable in the reception cavity.

Item 14: The portable device of item 13, wherein:
the test chamber is disposable and single-use.

Item 15: The portable device of item 13, further comprising:
a disposable cartridge removably positionable in the reception cavity, the cartridge comprising the test chamber and an inlet passage, the inlet passage sized to receive at least a portion of the probe, the inlet passage having an upstream end opposite a downstream end, the downstream end comprising the membrane.

Item 16: The portable device of item 1, further comprising:
at least one second test chamber, each second test chamber containing a respective liquid volume of test solution, and each second test chamber sealed by a respective pierceable membrane wall.

Item 17: The portable device of item 1, wherein:
the probe comprises a probe shaft having a pointed probe shaft end for piercing the membrane wall.

Item 18: The portable device of item 17, wherein:
the probe shaft is retractable, the probe shaft having an extended position and a retracted position.

Item 19: The portable device of item 8, wherein:
the probe comprises a probe shaft having a pointed probe shaft end for piercing the membrane wall,
the probe shaft is retractable, the probe shaft having an extended position and a retracted position
the probe shaft at least partially interferes with the sensor detecting the one or more characteristics when the probe extends into the test chamber and the probe shaft is in the extended position, and
interference by the probe shaft of detection by the sensor is at least partially reduced when the probe extends into the test chamber and the probe shaft is in the retracted position.

Item 20: The portable device of item 17, wherein:
the probe shaft end has at least one of shape and surface features that promote sampling of food.

Item 21: The portable device of item 17, wherein:
the probe comprises a lumen and a retractable plunger in the lumen.

Item 22: The portable device of item 17, wherein:
the probe shaft is porous.

Item 23: The portable device of item 17, wherein:
the probe shaft is pitted.

Item 24: The portable device of item 17, wherein:
the probe shaft is abrasive.

Item 25: The portable device of item 17, wherein:
the probe shaft end comprises a cavity.

Item 26: A method of detecting an analyte associated with an organic molecule in a liquid and/or solid substance, the method comprising:
piercing a test chamber wall with a probe to deposit a sample from the probe into a liquid volume of test solution including an analytical reagent contained in the test chamber;
mixing the sample with the test solution to form a test mixture in the test chamber; and
sensing one or more characteristics of the test mixture in the test chamber indicative of a reaction between the analyte and the analytical reagent.

Item 27: The method of item 26, further comprising:
exciting the one or more characteristics of the test mixture in the test chamber.

Item 28: The method of item 27, wherein:
exciting the one or more characteristics of the test mixture comprises exposing the test mixture in the test chamber to one or more of optical radiation and a magnetic field.

Item 29: The method of item 26, further comprising:
after said sensing, disposing of the test chamber.

Item 30: The method of item 26, further comprising, before said piercing:
sensing the one or more characteristics of the test solution.

Item 31: The method of item 30, further comprising, before said piercing:
exciting the one or more characteristics of the test solution.

Item 32: The method of item 30, further comprising:
comparing the one or more sensed characteristics of the test mixture to the one or more sensed characteristics of the test solution to determine whether the analyte is present in the sample.

Item 33: The method of item 32, further comprising:
if the analyte is determined to be present in the sample, then displaying on a display an indication that an organic molecule associated with the analyte is present in the sample.

Item 34: The method of item 32, further comprising:
if the analyte is determined to be absent from the sample, then displaying on a display an indication that an organic molecule associated with the analyte is absent from the sample.

Item 35: The method of item 26, further comprising:
piercing a substance with the probe to collect the sample in or on the probe.

Item 36: The method of item 26, wherein:
mixing the sample with the test solution comprises agitating the test solution.

Item 37: The method of item 36, wherein:
agitating the test solution comprises agitating the test chamber.

Item 38: The method of item 36, wherein:
agitating the test solution comprises reciprocating at least a probe shaft of the probe in the test chamber.

Item 39: The method of item 26, wherein:
said piercing the test chamber wall with the probe, comprises a probe shaft of the probe at least partially interfering with said sensing of the one or more characteristics of the test mixture, and
the method further comprises retracting the probe shaft thereby reducing interference by the probe shaft with said sensing of the one or more characteristics of the test mixture.

Item 40: The method of item 26, wherein:
piercing the test chamber wall comprises the test chamber wall removing samples from the probe.

Item 41: The method of item 26, further comprising:
  inserting the test chamber into a reception cavity aligned with an excitation source and a sensor.
Item 42: An organic molecular sensing system comprising:
  a portable device for detecting an analyte associated with a target organic molecule in a liquid and/or solid substance;
  a computing device coupled to the portable device to receive sensor data relating to one or more tests of the substance, wherein the computing device is operable to analyze the sensor data to produce test results corresponding to the presence of the analyte in the substance.
Item 43: The system of item 42, further comprising:
  a server device in communication with the computing device to receive test results, location information and/or contextual information.
Item 44: An organic molecular sensing system comprising:
  a portable device for detecting an analyte associated with a target organic molecule in a liquid and/or solid substance, wherein the portable device is operable to produce test results corresponding to the presence of the analyte in the substance;
  a computing device coupled to the portable device to receive test results corresponding to the presence of the analyte in the substance.
Item 45: The system of item 44, further comprising:
  a server device in communication with the computing device to receive test results, location information and/or contextual information.

The invention claimed is:
1. A portable device for detecting an analyte associated with a target organic molecule in a liquid and/or solid substance, the device comprising:
  a test chamber containing a liquid volume of test solution including an analytical reagent selected to react with the analyte, the test chamber sealed by a pierceable membrane wall;
  a probe removably positionable to pierce the membrane wall to deposit a sample in the test chamber to form a test mixture with the test solution;
  an excitation source to excite at least one characteristic of the test mixture, wherein the at least one characteristic includes one or more of magnetic, electrical, and optical characteristics; and
  a sensor configured to detect a temporal pattern of the at least one characteristic of the test mixture in the test chamber, wherein said temporal pattern comprises a variation in the at least one characteristic of the test mixture across a period of time, which is indicative of a reaction between the analyte and the analytical reagent.
2. The portable device of claim 1, wherein:
  the excitation source includes at least one of a light source, an electric field source, an electric current source, and a magnetic field source.
3. The portable device of claim 1, further comprising:
  a processor communicatively coupled to the sensor to assess whether the sample contains the analyte based at least in part on the detected at least one characteristic.
4. The portable device of claim 1, further comprising:
  a display controllable to indicate the presence of the analyte.
5. The portable device of claim 1, further comprising:
  a battery electrically connected to the sensor.
6. The portable device of claim 1, wherein:
  the test chamber has an illumination window and a sensor window,
  the excitation source comprises a light source directed to illuminate at least a portion of the test chamber through the illumination window, and
  the sensor comprises an optical sensor directed to detect optical radiation from the test chamber through the sensor window.
7. The portable device of claim 1, wherein:
  the test chamber contains between 1 µL and 250 µL of the test solution.
8. The portable device of claim 1, wherein:
  the test chamber has a volume of less than 1 mL.
9. The portable device of claim 6, wherein:
  the light source emits optical radiation having one or more first wavelengths, and
  the optical sensor detects optical radiation having one or more second wavelengths different from the one or more first wavelengths.
10. The portable device of claim 9, wherein:
  the one or more second wavelengths are greater than the one or more first wavelengths.
11. The portable device of claim 1, further comprising:
  a body containing the sensor, and a reception cavity, wherein the test chamber is removably positionable in the reception cavity.
12. The portable device of claim 11, wherein:
  the test chamber is disposable and single-use.
13. The portable device of claim 11, further comprising:
  a disposable cartridge removably positionable in the reception cavity, the cartridge comprising the test chamber and an inlet passage, the inlet passage sized to receive at least a portion of the probe, the inlet passage having an upstream end opposite a downstream end, the downstream end comprising the membrane.
14. The portable device of claim 1, further comprising:
  at least one second test chamber, each second test chamber containing a respective liquid volume of test solution, and each second test chamber sealed by a respective pierceable membrane wall.
15. The portable device of claim 1, wherein:
  the probe comprises a probe shaft having a pointed probe shaft end for piercing the membrane wall.
16. The portable device of claim 15, wherein:
  the probe shaft is retractable, the probe shaft having an extended position and a retracted position.
17. The portable device of claim 6, wherein:
  the probe comprises a probe shaft having a pointed probe shaft end for piercing the membrane wall,
  the probe shaft is retractable, the probe shaft having an extended position and a retracted position
  the probe shaft at least partially interferes with the sensor detecting the one or more characteristics when the probe extends into the test chamber and the probe shaft is in the extended position, and
  interference by the probe shaft of detection by the sensor is at least partially reduced when the probe extends into the test chamber and the probe shaft is in the retracted position.
18. The portable device of claim 15 wherein the probe has at least one feature selected from the group consisting of:
  the probe shaft has at least one of shape and surface features that promote sampling of food:
  the probe comprises a lumen and a retractable plunger in the lumen;

the probe shaft is porous;
the probe shaft is abrasive;
the probe shaft is pitted; and
the probe shaft comprises a cavity.

19. The portable device of claim 3, wherein:
the processor is communicatively coupled to the sensor and programmed to assess whether the sample contains the analyte based at least in part on a detected temporal pattern of the at least one characteristic of the test mixture.

20. The portable device of claim 1, wherein:
the temporal pattern comprises optical radiation at one or more first wavelengths followed by optical radiation at one or more second wavelengths.

\* \* \* \* \*